(12) United States Patent
Hamilton

(10) Patent No.: US 10,109,180 B1
(45) Date of Patent: *Oct. 23, 2018

(54) WIRELESS HALL LIGHT BOX

(71) Applicant: David L. Hamilton, Royal Oak, MI (US)

(72) Inventor: David L. Hamilton, Royal Oak, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/785,709

(22) Filed: Oct. 17, 2017

Related U.S. Application Data

(63) Continuation-in-part of application No. 15/667,916, filed on Aug. 3, 2017, now Pat. No. 10,008,103.

(51) Int. Cl.
| | |
|---|---|
| G08B 25/14 | (2006.01) |
| G08B 7/06 | (2006.01) |
| G08B 29/10 | (2006.01) |
| G16H 40/20 | (2018.01) |

(52) U.S. Cl.
CPC ............... *G08B 25/14* (2013.01); *G08B 7/06* (2013.01); *G08B 29/10* (2013.01); *G16H 40/20* (2018.01)

(58) Field of Classification Search
CPC .... G08B 25/10; G08B 25/008; G08B 25/016; G08B 19/00; G08B 3/1016
USPC ........................................................ 340/506
See application file for complete search history.

(56) References Cited

U.S. PATENT DOCUMENTS

| | | | | |
|---|---|---|---|---|
| 8,344,860 B2* | 1/2013 | Collins, Jr. | ........... | A61B 5/1115 340/286.07 |
| 8,384,526 B2* | 2/2013 | Schuman, Sr. | ........ | G08B 5/222 340/286.07 |
| 2002/0126157 A1* | 9/2002 | Farago | ................... | G01D 4/002 715/810 |
| 2016/0116183 A1* | 4/2016 | Lazar | ................. | G05D 23/1905 236/1 C |

* cited by examiner

*Primary Examiner* — Omar Casillashernandez
(74) *Attorney, Agent, or Firm* — Christopher P. Maiorana, PC

(57) ABSTRACT

An apparatus includes a wireless transceiver and a processor. The wireless transceiver may be configured to communicate wirelessly via a wireless network with an annunciator remotely located from the apparatus and a plurality of call light boxes remotely located from the apparatus. The processor may be configured to (i) control reception of an alarm message from one or more of the call light boxes in response to an event, (ii) illuminate a hall indicator in response to reception of the alarm message, (iii) receive a cancellation message from at least one of (a) one or more of the call light boxes and (b) the annunciator that cancels the event, and (iv) extinguish the hall indicator in response to cancellation of the event. The hall indicator may change color over time until the event is canceled.

18 Claims, 12 Drawing Sheets

WIRELESS HALL LIGHT BOX

This application relates to U.S. Ser. No. 15/667,916, filed Aug. 3, 2017, which is incorporated by reference in its entirety.

FIELD OF THE INVENTION

The invention relates to alert systems generally and, more particularly, to a method and/or apparatus for implementing a wireless hall light box.

BACKGROUND

Buildings used for assisted living, nursing homes, rehabilitation centers and hospitals include a conventional call light system that allows residents of the building to request help from the staff in the building. The call light systems are hardwired into the buildings and controlled by a central panel. As a result, the call light systems are difficult to upgrade and repair. Furthermore, a failure of the central panel renders the entire call light system inoperable.

It would be desirable to implement a wireless hall light box.

SUMMARY

The invention concerns an apparatus including a wireless transceiver and a processor. The wireless transceiver may be configured to communicate wirelessly via a wireless network with an annunciator remotely located from the apparatus and a plurality of call light boxes remotely located from the apparatus. The processor may be configured to (i) control reception of an alarm message from one or more of the call light boxes in response to an event, (ii) illuminate a hall indicator in response to reception of the alarm message, (iii) receive a cancellation message from at least one of (a) one or more of the call light boxes and (b) the annunciator that cancels the event, and (iv) extinguish the hall indicator in response to cancellation of the event. The hall indicator may change color over time until the event is canceled.

BRIEF DESCRIPTION OF THE FIGURES

Embodiments of the invention will be apparent from the following detailed description and the appended claims and drawings in which:

DETAILED DESCRIPTION OF THE EMBODIMENTS

Embodiments of the present invention include providing a wireless hall light box that may (i) easily repaired, (ii) easy to upgrade, (iii) be fault tolerant, (iv) change colors of active alarm indicators over time until the active alarms are answered, (v) change sounds of active alarm indicators over time until the active alarms are answered, (vi) provide reports to kitchen staff, (vii) provide reports to maintenance staff, (viii) provide reports to management, (ix) log alarm response times, (x) log identification of staff that responded to an alarm, (xi) sort a list of active alarms on an annunciator by time and/or (xii) sort a list of active alarms on the annunciator by priority.

Embodiments of the present invention generally provide a distributed nurse call light system. The system is generally implemented with multiple, independent processors at strategic locations throughout a building (e.g., assisted living, nursing homes, rehabilitation centers, hospitals, etc.). The processors may communicate with each other and a server computer through one or more wireless networks. Multiple call light boxes, each containing one or more processors, may be located in each residential room of the building. Typically a call light box is located in at least each bedroom, bathroom and living area of the residential rooms. The call light boxes are generally position for ease of access by the residents (or patients). Multiple hall light boxes, each containing one or more processors, may be located outside hall doors to the residential rooms. One or more annunciator panels, each containing one or more processors, may be located at one or more nurse stations in the building. At least one pager system in the building may each contain one or more processors.

In various embodiments, an alarm indicator on the annunciators, hall light boxes and call light boxes may slowly change color (e.g., from white to red) over time (e.g., after a defined time) to indicate a time priority of the active alarms in a queue (or list). The annunciator panels, the call light boxes and the hall light boxes may also change sound and/or colors to indicate a length of time that the alarms have been active (or unanswered). The changing colors and/or sounds generally aid the staff in visually and/or audibly determining the alarms that have been active the longest. The alarm that has been active the longest may be at top of a list of rooms presented by the annunciator panel. The list may help prevent the staff from answering a low-priority alarm in a nearby room before answering a high-priority alarm in a room further away.

Figure 1:
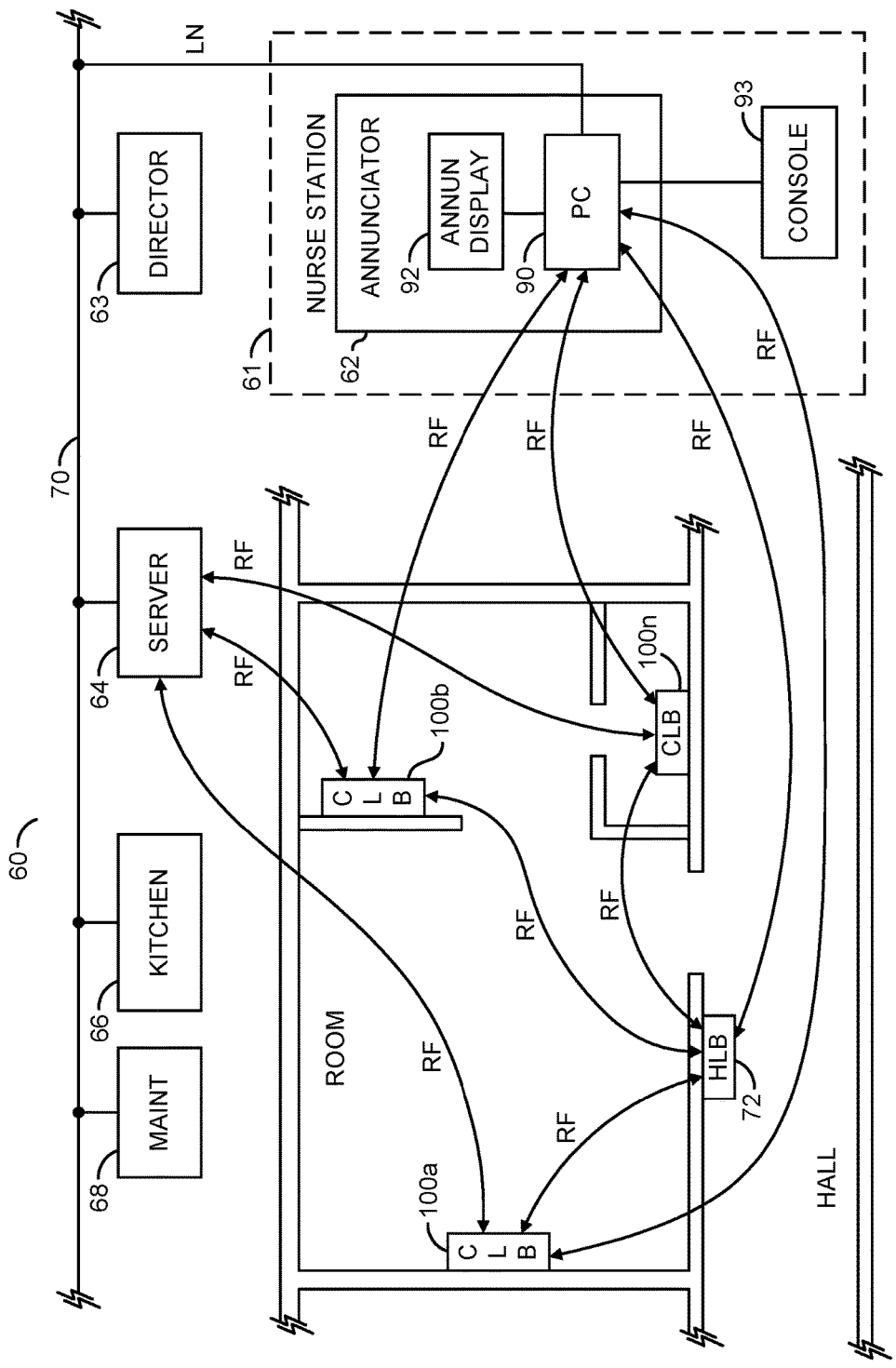
FIG. 1 is a diagram of a system.

Referring to FIG. 1, a diagram of an example implementation of a system 60 is shown. The system (or apparatus or assembly) 60 generally implements a distributed nurse call system. The system 60 generally comprises one or more blocks (or stations, one shown) 61, one or more blocks (or circuits, one shown) 62, a block (or circuit) 63, a block (or circuit) 64, a block (or circuit) 66, a block (or circuit) 68, a network (or communication channel) 70, multiple blocks (or circuits, one shown) 72 and multiple blocks (or circuits) 100a-100n. Each circuit 62 generally comprises a block (or circuit) 90, a block (or circuit) and a block (or circuit) 93. The circuits 62 to 93 may represent modules and/or blocks, embodiments of which include one or more of hardware circuitry and executable code (e.g., software, microcode, programming instructions, firmware, etc.) in a storage device used by the hardware circuitry.

A signal (e.g., LN) may be exchanged among the circuits 63, 64, 66, 68 and 90. The signal LN may present bidirectional data flow in the network 70. A signal (e.g., RF) may be exchanged among the circuits 64, 72, 74 (FIG. 2), 76 (FIG. 2), 90 and 100a-100n. The signal RF may represent a bidirectional data flow in a radio frequency wireless network. In various embodiments, the wireless network may be configured to provide wireless communication by one or more wireless protocols such as Bluetooth®, ZigBee®, Institute of Electrical and Electronics Engineering (IEEE) 802.11, IEEE 802.15, IEEE 802.15.1, IEEE 802.15.2, IEEE 802.15.3, IEEE 802.15.4, IEEE 802.15.5, IEEE 802.20, GSM, CDMA, GPRS, UMTS, CDMA2000, 3GPP LTE, 4G/HSPA/WiMAX and/or SMS. Other wireless networks may be implemented to meet the design criteria of a particular application.

Each station 61 may implement a nurse station. A nurse station 61 may be located near a group of corresponding rooms. Each nurse station 61 may provide equipment for one or more staff members to monitor the residents (or patients) in the nearby group of rooms.

The circuit 62 may implement an annunciator at a corresponding nurse station 61. The annunciator 62 is generally operational to present visual and/or acoustic status information for each room to the staff members. In various embodiments, the visual information may be presented in the form of a list on a display (e.g., the circuit 92). The list may show higher priority active alarms in lines nearest the top. A color of each line may change over time the longer an alarm is active. In some embodiments, the acoustic information may be presented in the form of tones or prerecorded messages from the display. The tones/messages may be different from each other to uniquely identify the different types of active alarms. The tones/messages may change over time the longer an alarm is active. In various embodiments, the annunciator 62 may be operational to remotely cancel active alarms.

The circuit 63 may implement a director computer. The director computer 63 is generally operational to provide remote access to the circuits 62, 64, 66, 68 and 100a-100n. The director computer 63 may be used by a Director of Health Services (or Director of Nursing). In various embodiments, the Director of Nursing and/or other select staff members may use the director computer 63 to remotely access the annunciators 62 and/or the circuits 64, 66, 68 and 100a-100n of the entire system 60. In various embodiments, the director computer 63 may be able to monitor all call lights activated in the facility. In some embodiments, the director computer 63 may be able to select among the circuits 100a-100n to see a live view of a video camera built into each circuit 100a-100n. The director computer 63 may be a secured system.

The circuit 64 may implement a server computer. The server computer 64 is generally operational to store data, retrieve and transmit stored data, process data, communicate with other devices, coordinate the flow of information within the system 60 and/or facilitate communications outside the system 60. In various embodiments, the server computer 64 may communicate with the individual circuits 100a-100n and the circuit 72 via the wireless network. In some instances, information received from the circuits 100a-100n and the circuit 72 may be converted into and/or attached to emails transmitted to other machines, such as the annunciator 62, the circuit 66, the circuit 68 and any other computer coupled to the network 70.

The circuit 66 may implement a computer located in a kitchen (or dietary) area of the building. The kitchen computer 66 is generally operational to present messages received on the network 70 to the kitchen staff. The messages may include requests from the residents concerning dietary situations.

The circuit 68 may implement a computer located in a maintenance area of the building. The maintenance computer 68 is generally operational to present messages received on the network 70 to the maintenance staff. The maintenance computer 68 may also be operational to request log information, test data and request other maintenance type data from the server computer 64, the annunciator 62, the circuit 72, the circuits 100a-100n and other equipment accessible over the network 70.

The network 70 may implement a wired network. The wired network 70 is generally operational to provide bidirectional communications between the annunciator 62, the director computer 63, the server computer 64, the kitchen computer 66, the maintenance computer 68 and any other equipment coupled to the wired network 70. In various embodiments, the wired network 70 may be implemented as a local area network or a wide area network. The wired network 70 may include, but is not limited to, an Ethernet network, the Internet, a Universal Serial Bus network and a fiber optic network. Other networks may be implemented to meet the design criteria of a particular application.

The circuit 72 may implement a hall light box. The hall light box 72 is generally operational to present visual and/or acoustic status information for a corresponding room to anyone in the hallway. In various embodiments, the visual information may be presented in the form of a visible indicator and/or textual (e.g., alphanumeric) message on a display. Where the visual information implements an alarm, a color of the visible indicator/message may change over time the longer an alarm is active. In some embodiments, the acoustic information may be presented in the form of a tone or prerecorded messages. Where the acoustic information implements an alarm, the tones/messages may be different from each other to uniquely identify the different types of active alarms. The tones/messages may change over time the longer an alarm is active. In some environments, one or more hall light boxes 72 may be located at information centers, such as kiosks located throughout the facility.

The circuit 90 may implement a personal computer (PC). The personal computer 90 may be operational to communicate with the circuits 100a-100n and the hall light boxes 72 via the wireless network. The personal computer 90 may also be operational to communicate with the director computer 63, the server computer 64, the kitchen computer 66, the maintenance computer 68 and any other equipment coupled to the wired network 70. The personal computer 90 may provide bidirectional communications with the circuit 92.

The circuit 92 may implement an annunciator panel. The annunciator panel 92 may be operational to display the status list of the rooms to the staff, display video received from the call light boxes 100a-100n, receive switch activation inputs from the staff, play audio information, and receive sounds (e.g., voice) from the staff. In some embodiments, the annunciator display 92 may be implemented a liquid crystal display for low power consumption. The annunciator display 92 may be configured to go into a sleep mode to conserve power if no alarms are active.

The circuit 93 may implement a console. The console 93 may be located in or near the nurse station 61. The console 93 may be operational to provide two-way communications between the nurse station 61 and the circuits 100a-100n.

Each circuit 100a-100n may implement a call light box. The call light boxes 100a-100n are generally operational to provide input sensors and output actuators to the resident, the staff and the local environment. The input sensor may include multiple switches (e.g., a call switch, a code blue switch, etc.). A video camera may provide visual motion pictures of the area proximate a front of the respective call light box 100a-100n. Other input sensors may include a card reader that may be operational to receive an identification number (or code) from an identification (or name) badge swiped in proximity to the card reader. Some sensors may monitor the local environment (e.g., temperature, humidity and carbon monoxide (CO) levels). Other sensors may be responsive to local sounds. The output actuators may include a display, a speaker and a night light.

The system 60 may have a decentralized data processing and data storage capability. If the annunciator 62, the director computer 63, the server computer 64, some hall light boxes 72 and/or some call light boxes 100a-100n fail, the rest of the system 60 may continue to operate. For example, if the annunciator 62 fails, the call light boxes 100a-100n and the hall light boxes 72 may continue to communicate with each other. Any alarm initiated by a call light box 100a-100n may be transferred to the corresponding hall light box 72, and the hall light box 72 responds according to the received directions. In another example, if the annunciator 62 and/or the server computer 64 fails, the hall light boxes 72 and the call light boxes 100a-100n generally buffer any information destined for the annunciator 62 and/or the server computer 64. Once the annunciator 62 and/or server computer 64 is back online, the buffered information may be transferred to the annunciator 62 and/or server computer 64.

Figure 2:
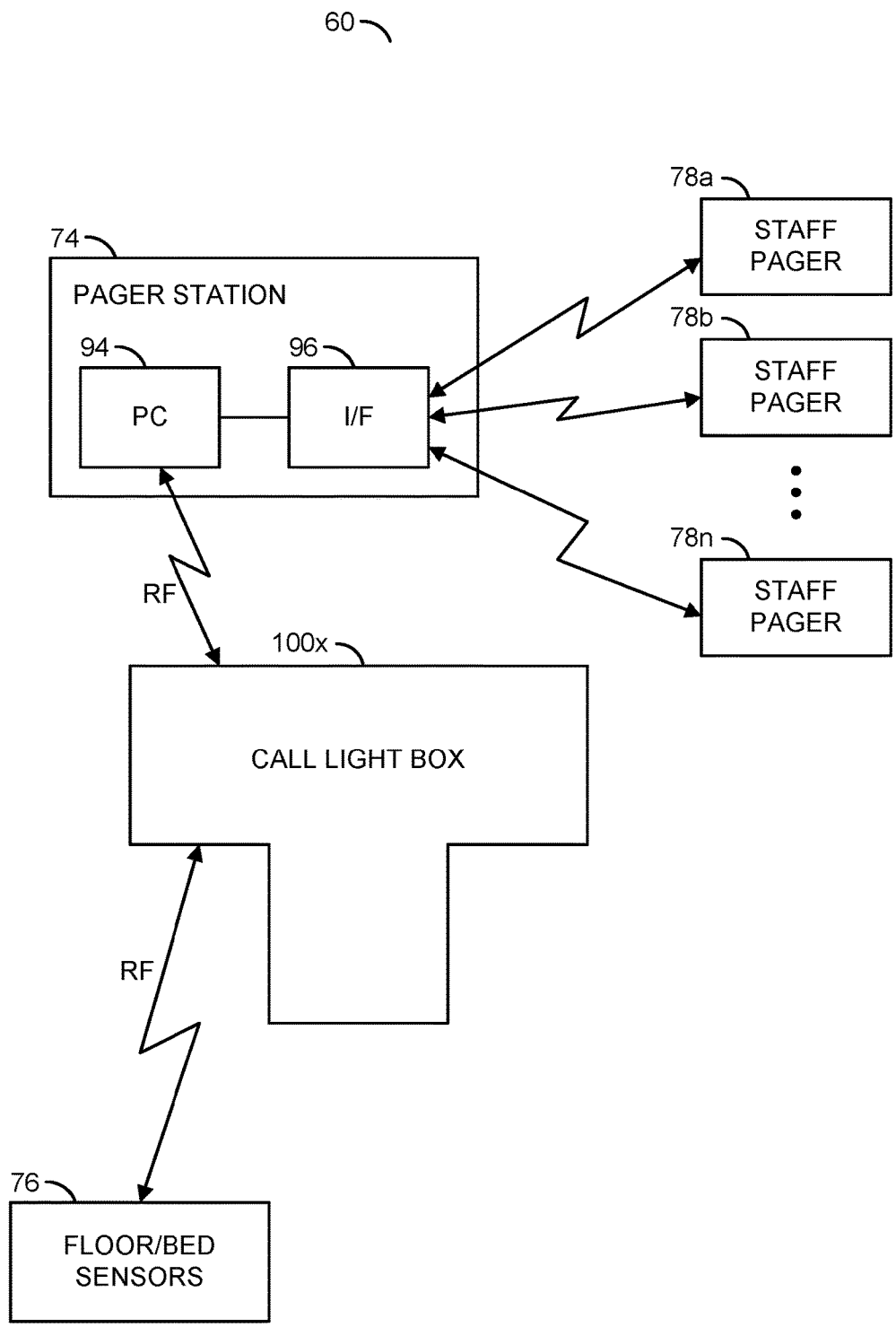
FIG. 2 is a diagram of another portion of the system shown in FIG. 1.

Referring to FIG. 2, a diagram of a portion of the system 60 is shown. The system 60 may further comprise a block (or circuit 74, one or more blocks (or circuits, one shown), 76 multiple blocks (or circuits) 78a-78n and a call light box 100x. The circuit 72 generally comprises a block (or circuit) 94 and a block (or circuit) 96. The call light box 100x may be representative of each of the call light boxes 100a-100n. The circuits 74-96 may represent modules and/or blocks, embodiments of which include one or more of hardware circuitry and executable code (e.g., software, microcode, programming instructions, firmware, etc.) in a storage device used by the hardware circuitry. The circuit 74 may implement a pager station. The pager station 74 is generally operational to exchange messages with the call light boxes 100a-100n via the wireless network. The pager station 74 may also be operational to exchange messages with the circuit 78a-78n via a pager network.

The circuit 76 may implement one or more of a floor sensor and/or a bed sensor. A floor sensor 76 is generally operational to sense when a person is standing, resting and/or walking on the sensor 76. The floor sensor 76 is typically located adjacent to a bed in the bedroom.

When a floor sensor 76 next to a bed identifies a weight, a trigger message may be sent via the wireless network to the corresponding call light box 100x (e.g., the call light box 100a-100n in near physical proximity to the floor sensor 76). The call light box 100x may interpret the trigger message as a resident getting out of bed and/or another person (e.g., a staff member or a guest) standing next to the bed. The call light box 100x may subsequently send a message to the annunciator 62 and/or the server computer 64 that the floor sensor 76 has been triggered. When the weight is removed from the floor sensor 76, the floor sensor 76 may send another message to the call light box 100x. The call light box 100x may send a follow-up message to the annunciator 62 and/or the server computer 64.

When a bed sensor 76 senses that a weight has been removed, another trigger message may be sent via the wireless network to the corresponding call light box 100x (e.g., the call light box 100a-100n in near physical proximity to the bed sensor 76). The call light box 100x may interpret the trigger message as a resident getting out of bed. The call light box 100x may subsequently send a message to the annunciator 62 and/or the server computer 64 that the bed sensor 76 has been triggered. When the weight is returned to the bed sensor 76, the bed sensor 76 may send another message to the call light box 100x. The call light box 100x may send a follow-up message to the annunciator 62 and/or the server computer 64.

In various embodiments, the messages generated by the floor/bed sensors 76 may cause the processor in the call light box 100x to generate and transmit a call light message. Cancellation of the call light message may be achieved by swiping a staff card at the call light box 100x. In some embodiments, the call light message may be cancelled remotely from the annunciator 62.

Each circuit 78a-78n may implement a portable pager. The pagers 78a-78n are generally operational to display messages received from the pager station 72 to the staff members carrying the pagers. In various embodiments, the pagers 78a-78n may generate a visible message and a tone when a new message is received.

The circuit 94 may implement a personal computer. The personal computer 94 may be operational to communicate with the call light boxes 100a-100n (e.g., 100x) via the wireless network. The personal computer 94 may provide bidirectional communications with circuit 96 to relay messages from the call light boxes 100a-100n to the pagers 78a-78n.

The circuit 96 may implement a pager interface circuit. The pager interface circuit 96 is generally operational to communicate with the pagers 78a-78n via a wireless pager network. The pager interface circuit 96 may be in bidirectional communication with the personal computer 94.

Figure 3:
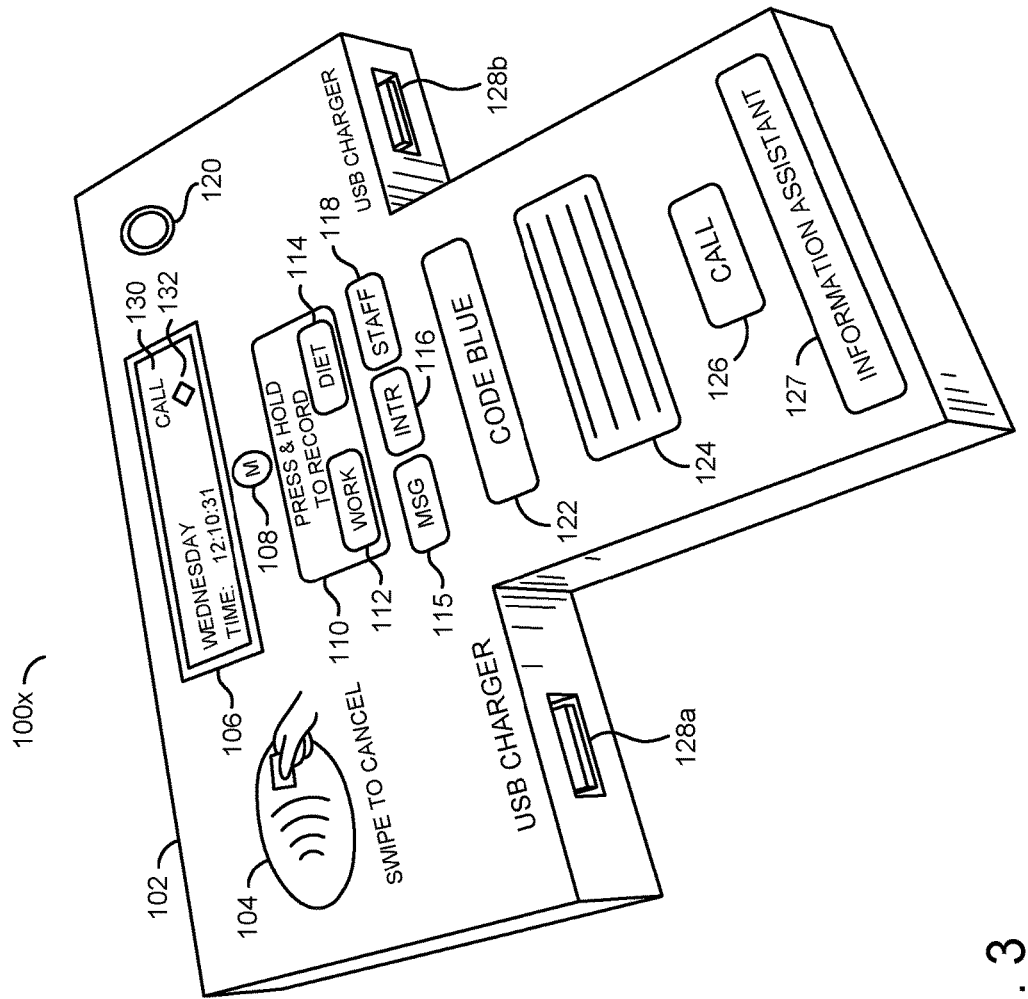
FIG. 3 is a perspective view of a call light box.

Referring to FIG. 3, a perspective view of the call light box 100x is shown. The call light box 100x generally comprises a housing (or case) 102, a block (or circuit) 104, a block (or circuit) 106, a block (or circuit) 108, a block (or circuit) 110, a block (or circuit) 112, a block (or circuit) 114, a block (or circuit) 115, a block (or circuit) 116, a block (or circuit) 118, a block (or circuit) 120, a block (or circuit) 122, a block (or circuit) 124, a block (or circuit) 126, a block (or circuit) 127, one or more blocks (or circuits, two shown) 128a-128b. The circuits 102-128b may represent modules and/or blocks, embodiments of which include one or more of hardware circuitry and executable code (e.g., software, microcode, programming instructions, firmware, etc.) in a storage device used by the hardware circuitry.

The circuit 104 may implement a card reader. The card reader 104 may be operational to receive an identification number (or code) from an identification (or name) badge swiped in proximity to the card reader 104. The identification number may be used to cancel all active alarms in progress. In various embodiments, the card reader 104 may be implemented as one or more of a radio-frequency identification card, a magnetic card, and a barcode card.

The circuit 106 may implement a display. The display may be operational to present alphanumeric and/or graphic information. In various embodiments, the display 106 may be implemented as a liquid crystal display. In some embodiments, the display 106 may include a touch screen capability. The display 106 may be used for resident orientation with time, date and/or current outside weather conditions, built into the call light boxes 100a-100n. The alphanumeric information may include general information (e.g., date, time, room temperature, etc.) In some embodiments, the alphanumeric information may include an alarm indicator, such as a name 130 of a highest priority active alarm (e.g., BLUE, INTR, or CALL). The graphic information may include general information (e.g., weather symbols, analog clock face, etc.) In various embodiments, the graphic information may include the alarm indicator, such as a graphic symbol 132 for either the highest priority active alarm or a different symbol for each active alarm. The color of the textual message and/or graphical information for the active alarms may change over time as the duration of the active alarm lengthens.

The circuit 108 may implement a microphone. The microphone 108 may be operational to record sounds from the environment around the call light box 100x. The sounds may be available to the internal circuitry and software programs of the call light box 100x, such as an information assistant capability. The microphone 108 may also be operational to detect a clapping sound originating nearby. In various embodiments, the microphone 108 may be implemented as an omnidirectional microphone.

The circuit 110 may implement a set of service switches. The service switches may be operational to record verbal requests for service from the staff. The verbal requests may be sensed with the microphone 108.

The circuit 112 may implement a work order switch. The work order switch 112 may be operational to initiate a recording and processing of a verbal work order request made by the residents and/or the staff. The work order switch 112 may be implemented as a momentary push switch that starts the recording when pressed and ends the recording when released.

The circuit 114 may implement a dietary switch. The dietary switch 114 may be operational to initiate a recording and processing of a verbal dietary request made by the residents and/or the staff. The dietary switch 114 may be implemented as a momentary push switch that starts the recording when pressed and ends the recording when released.

The circuit 115 may implement a message switch. The message switch 115 may be operational to play an audio and/or visual message at the call light box 100x when pressed. The audio and/or visual messages may be generated by the staff members, for example a receptionist, and directed to a particular resident/patient.

The circuit 116 may implement an intermediate level alarm switch. The intermediate switch 116 may be operational to initiate an intermediate-level alarm to the staff and to the server computer 64. The intermediate switch 116 may be implemented as a momentary push switch that initiates the intermediate-level alarm when pressed. Cancellation of the intermediate-level alarm may be achieved by swiping an authorized identification badge at the card reader 104. In some embodiments, pressing and holding the intermediate switch 116 beyond a predetermined period may cause the call light boxes 100a-100n to treat the intermediate-level alarm as a higher-level alarm (e.g., a code blue-level alarm).

The circuit 118 may implement a staff-only switch. The staff-only switch 118 may be operational to alert one or more staff members that non-emergency assistance is requested in the room where the staff-only switch 118 was pressed. The alert may be communicated through the pagers 78a-78n of the staff members. The staff-only switch 118 may be implemented as a momentary push switch and is intended to be used by staff members only.

The circuit 120 may implement a video camera. The camera 120 may be operational to capture video of the environment in front of the call light box 100x and generate a video signal. The video capture may be started upon the activation of at least the switch 122. In various embodiments, specific staff members, such as the Director of Nursing, may remotely access to the camera 120 to monitor patient care. Video capture initiated upon other switch activations may be implemented to meet the design criteria of a particular application.

The circuit 122 may implement a code blue alarm switch. The code blue switch 122 may be operational to initiate a top-level alarm to the staff and to the server computer 64. The code blue switch 122 may be implemented as a momentary push switch that initiates the top-level alarm when pressed. Cancellation of the top-level alarm may be achieved by swiping an authorized identification badge at the card reader 104.

The circuit 124 may implement a speaker. The speaker 124 is generally operational to generate audible sounds. The audible sounds may include verbal messages and/or tones. In some situations, the verbal messages may be prerecorded messages. In other situations, the verbal messages may be live messages. The tones may be sounded upon the activation of the code blue alarms, the intermediate alarms and/or the regular (or normal) alarms. The tones may be prioritized such that the higher-priority tones are sounded in favor of the lower-priority tones. The tones may change over time while the highest-priority alarm remains active. The tones may be extinguished after all of the alarms have been cancelled.

The circuit 126 may implement a normal call switch. The call switch 126 may be operational to initiate a normal-level alarm to the staff and to the server computer 64. The call switch 126 may be implemented as a momentary push switch that initiates the normal-level alarm when pressed. Cancellation of the normal-level alarm may be achieved by swiping an authorized identification badge at the card reader 104 and/or pressing the call switch 126 again. In various embodiments, a normal level alarm may be cancelled remotely from the annunciator 62. Multiple (e.g., 4) quick presses of the call switch 126 may trigger a text message sent to specific staff pagers indicating that assistance is requested in the specific room. In some embodiments, pressing and holding the call switch 126 beyond a predetermined period may cause the call light boxes 100a-100n to treat the low-level alarm as a higher-level alarm (e.g., an intermediate-level alarm).

The circuit 127 may implement an information assistant switch. The information assistant switch 127 may be operational to provide verbal assistance to questions asked by and/or orders presented by the residence and/or staff. For example, the orders may be to set alarms, turn on the call light, place work orders, place dietary order, and such. Feedback that the verbal message was received may be provided on the display 106. The information assistant capability may be implemented as part of commercially available systems, such as Google Home® (a registered trademark of Google, Inc.) and Amazon Alexa® (a registered trademark of Amazon Technologies, Inc.). Other information assistance systems may be implemented to meet the design criteria of a particular application.

Each circuit 128a-128b may implement a Universal Serial Bus (USB) port. The USB ports 128a-128b may be operational to provide electrical power. In various embodiments, the USB ports 128a-128b may be compatible with the USB, USB 2.0, USB 3.0 USB 3.1 and/or the USB-C standards.

Figure 4:
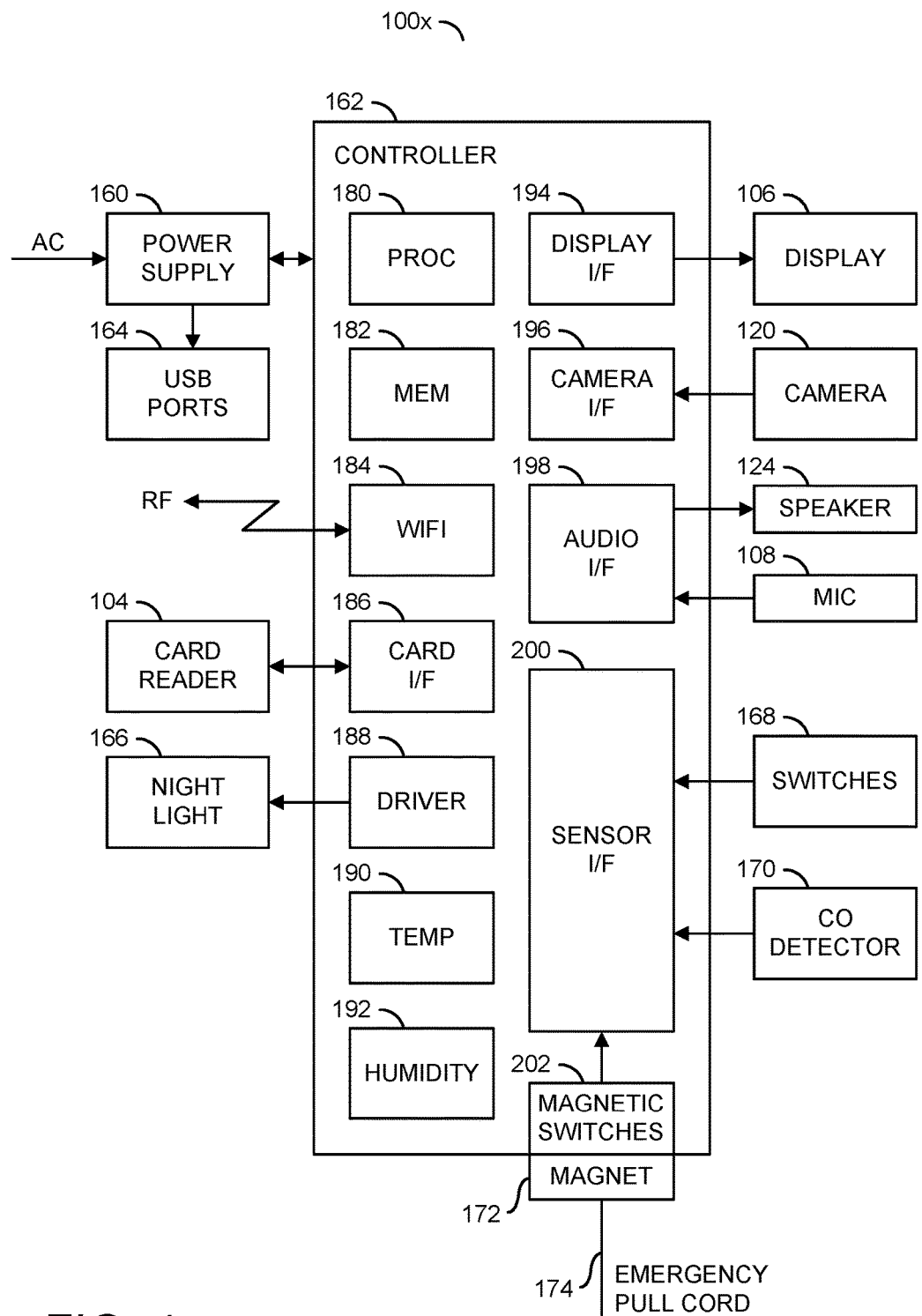
FIG. 4 is a diagram of the call light box.

Referring to FIG. 4, a diagram of an example implementation of the call light box 100x is shown. The call light box 100x generally comprises the card reader 104, the display 106, the microphone 108, the camera 120, a block (or circuit) 160, a block (or circuit) 162, a block (or circuit) 164, a block (or circuit) 166, a block (or circuit) 168, a block (or circuit) 170, a block (or circuit) 172 and a chord (or cable)

174. The circuit 162 generally comprises a block (or circuit) 180, a block (or circuit) 182, a block (or circuit) 184, a block (or circuit) 186, a block (or circuit) 188, a block (or circuit) 190, a block (or circuit) 192, a block (or circuit) 194, a block (or circuit) 196, a block (or circuit) 198, a block (or circuit) 200 and a block (or circuit) 202. The circuits 160-202 may represent modules and/or blocks, embodiments of which include one or more of hardware circuitry and executable code (e.g., software, microcode, programming instructions, firmware, etc.) in a storage device used by the hardware circuitry.

The circuit 160 may implement a power supply circuit. The power supply may receive signal (e.g., AC) carrying alternating current electrical power. The power supply circuit 160 may be operational to convert the AC power to direct current (DC) power. The DC power may be presented to the circuit 162 and the circuit 164.

The circuit 162 may implement a controller circuit. The controller 162 is generally operational to control the flow of information and operations of the call light box 100x. In various embodiments, the controller 162 may include one or more processors that implement a portion of the functionality of the call light box 100x in software (or code or firmware).

The circuit 164 may implement a USB circuit. The USB circuit 164 may be representative of the USB ports 128a-128b. The circuit 164 may be operational to provide electrical power to external devices plugged into the USB ports.

The circuit 166 may implement a night light. The night light 166 may be operational to generate a low-level light directed into the room. The night light 166 is commonly directed toward the floor. The night light 166 generally provides the light for safety purposes and to make it easy to locate the call light box 100x in a dark room.

The circuit 168 may implement a set of switches. The switches may include, but are not limited to the work switch 112, the dietary switch 114, the message switch 115, the intermediate switch 116, the staff-only switch 118, the code blue switch 122, the call switch 126 and the information assistant switch 127. Other switches may be implemented to meet the design criteria of a particular application.

The circuit 170 may implement a carbon monoxide (CO) detector. The carbon monoxide detector 170 is generally operational to sense a level of carbon monoxide in the atmosphere around the call light box 100x. The carbon monoxide level may be transferred to the controller 162.

The circuit 172 may implement a magnet. The magnet 172 may be operational to initiate a normal alarm when pulled away from the call light box 100x using the call light cord 174. Because the call light cord 174 may be magnetically connection to the call light box 100x, the call light cord 174 generally releases without damage when extended or pulled too far. In various embodiments, the call light cord 174 and the call switch 126 may be supplemented by a television remote control with a built-in call light button.

The circuit 180 may implement one or more processors (one shown). The processor 180 is generally operational to execute software to control the workings of the call light box 100x.

The circuit 182 may implement a memory circuit. The memory 182 is generally operational to store the software executed by the processor 180. In various embodiments, the memory 182 may be used to buffer information gathered by the call light box 100x but not yet transmitted to the annunciator 62, the server computer 64 and/or the pager station 74. In some embodiments, part or all of the memory 182 may be implemented as nonvolatile memory.

The circuit 184 may implement a wireless transceiver circuit. The wireless transceiver 184 may be operational to provide bidirectional communications between the call light box 100x and (i) a corresponding (or nearest) hall light box 72, (ii) the annunciator 62, (iii) the server computer 64 and (iv) the pager station 74.

The circuit 186 may implement a card reader interface circuit. The card reader interface circuit 186 is generally operational to power the card reader 104 and receive the data received by the card reader 104.

The circuit 188 may implement a driver circuit. The driver circuit 188 is generally operational to provide electrical power to the night light 166.

The circuit 190 may implement a temperature sensor. The temperature sensor 190 may be operational to sense a temperature of the environment around the call light box 100x.

The circuit 192 may implement a humidity sensor. The humidity sensor 192 may be operational to sense a humidity of the environment around the call light box 100x.

The circuit 194 may implement a display interface circuit. The display interface circuit 194 may be operational to control the display 106. Where the display 106 includes the touch screen capability, the display interface circuit 194 may be operational to provide the touch screen entries to the processor 180.

The circuit 196 may implement a camera interface circuit. The camera interface circuit 196 may be operational to control the camera 120.

The circuit 198 may implement an audio interface circuit. The audio interface circuit 198 may be operational to receive electrical signals generated by the microphone 108. The audio interface circuit 198 may also be operational to generate electrical signals that drive the speaker 124.

The circuit 200 may implement a sensor interface circuit. The sensor interface circuit 200 may be operational to sense the status of the switches 168 and 202. The sensor interface circuit 200 may also be operational to receive the carbon monoxide level sensed by the carbon monoxide detector 170.

The circuit 202 may implement a magnetic switch. The magnetic switch is generally operational to determine if the magnet 172 is present adjoining the housing 102 of the call light box 100x or has been pulled away from the housing 102. The state of the magnetic switch 202 may be presented to the sensor interface circuit 200.

Figure 5:
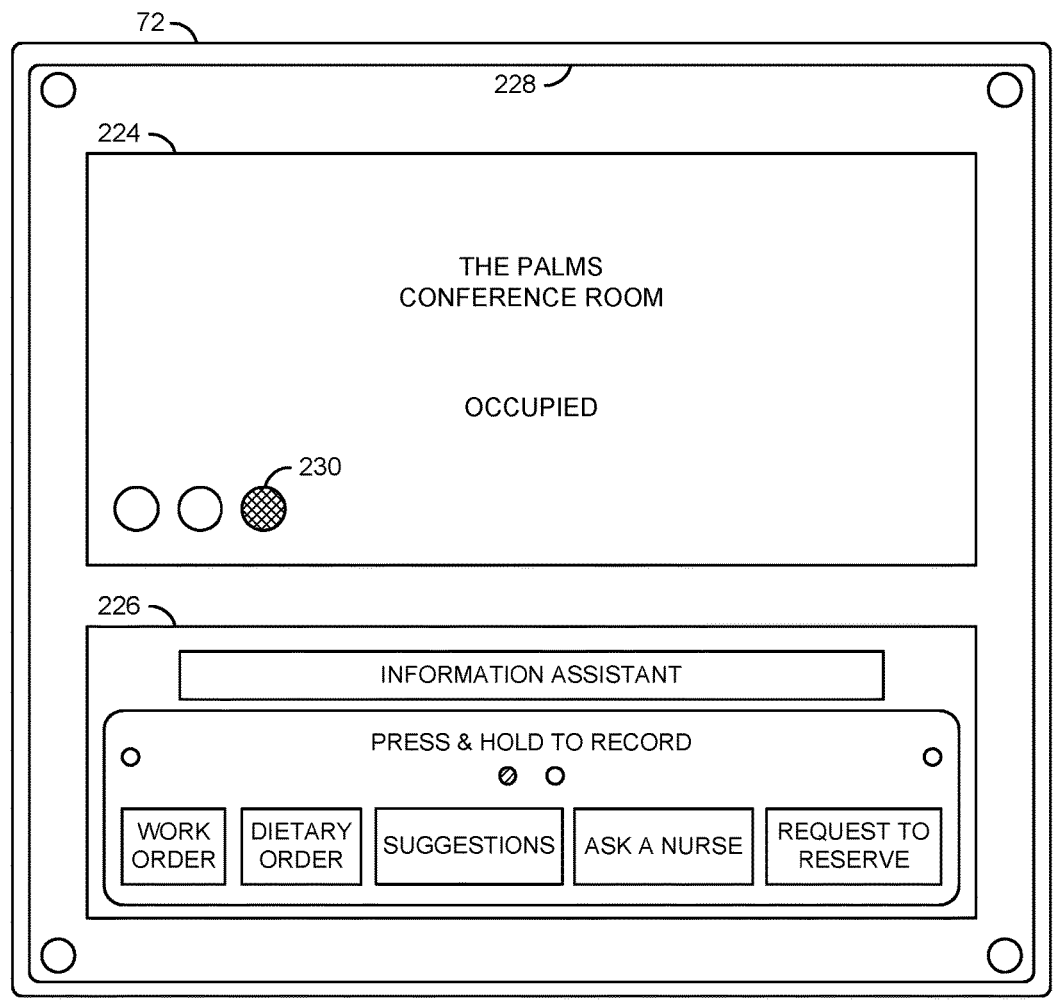
FIG. 5 is a view of a hall light box in accordance with an embodiment of the invention.

Referring to FIG. 5, a view of an example implementation of the hall light box 72 is shown in accordance with an embodiment of the invention. The hall light box 72 generally comprises a block (or circuit) 224, a block (or circuit) 226 and a block (or circuit) 228. The circuits 224-228 may represent modules and/or blocks, embodiments of which include one or more of hardware circuitry and executable code (e.g., software, microcode, programming instructions, firmware, etc.) in a storage device used by the hardware circuitry.

The circuit 224 may implement a display circuit. The display 224 may be operational to present alphanumeric, graphic information and/or menus 230. The menus 230 may be programmable via the server computer 64. The server computer 64 may also be used to change the names, positions, as such of information shown in the display 224.

The circuit 226 may implement a set of switches. The switches 226 may include, but are not limited to an intermediate switch, a code blue switch, a call switch, a work order switch, a dietary order switch, a suggestions switch, an ask-a-nurse switch, a request-to-reserve-a-room switch, and an information assistance switch. The switches 226 may be used by the staff to make changes to the display 224. The changes may include, but are not limited to, a conference room is occupied/unoccupied, and a room is reserved/not reserved. Other switches may be implemented to meet the design criteria of a particular application.

The work order switch may be operational to initiate a recording and processing of a verbal work order request made by the residents and/or the staff. The work order requests may be transferred via the wireless network to the server computer 64 and subsequently be related to the maintenance computer 68 (similar to the call light box 100). The work order switch may be implemented as a momentary push switch that starts the recording when pressed and ends the recording when released.

The dietary switch may be operational to initiate a recording and processing of a verbal dietary request made by the residents and/or the staff. The dietary requests may be transferred via the wireless network to the server computer 64 and subsequently be relayed to the kitchen computer 66 (similar to the call light box 100). The dietary switch may be implemented as a momentary push switch that starts the recording when pressed and ends the recording when released.

The suggestions switch may be operational to initiate a recording and processing of a verbal suggestion made by the residents and/or the staff. The verbal request may be transferred via the wireless network to the annunciator 62 and subsequently be relayed to the staff. The suggestion switch may be implemented as a momentary push switch that starts the recording when pressed and ends the recording when released.

The ask-a-nurse switch may be operational to initiate a recording and processing of a verbal question made by the residents. The verbal question may be transferred via the wireless network to the server computer 64 and subsequently be relayed to the staff. The ask-a-nurse switch may be implemented as a momentary push switch that starts the recording when pressed and ends the recording when released.

The request-to-reserve-a-room switch may be operational to initiate a recording and processing of a verbal request made by the staff. The verbal request may be transferred via the wireless network to the server computer 64 and subsequently be relayed to a receptionist. The receptionist may send one or more messages to the hall light box 72 to present a graphic symbol (or icon) on the display 224 that indicates that the room has been reserved or not reserved. The request-to-reserve-a-room switch may be implemented as a momentary push switch that starts the recording when pressed and ends the recording when released.

The information assistant switch may be operational to provide verbal assistance to questions ask by and/or orders presented by the residence and/or staff. For example, the orders may be to set alarms, turn on the call light, place work orders, place dietary order, and such. Feedback that the verbal message was received may be provided on the display 226. The information assistant capability may be implemented as part of commercially available systems, such as Google Home® and Amazon Alexa®. Other information assistance systems may be implemented to meet the design criteria of a particular application.

The circuit 228 may implement a hall indicator. The hall indicator 228 may be located on two or more sides (e.g., at least the vertical sides) of a frame of the hall light box 72 such that the hall indicator 228 is visible from up and down the hall. In some embodiments, the hall indicator 228 may be used in place of common corridor nurse call light indicators to help give the facilities a less institutional appearance. In other embodiments, such as in an office setting, the hall indicator 228 may be used as an ambient light and/or a room used/empty indicator.

Figure 6:
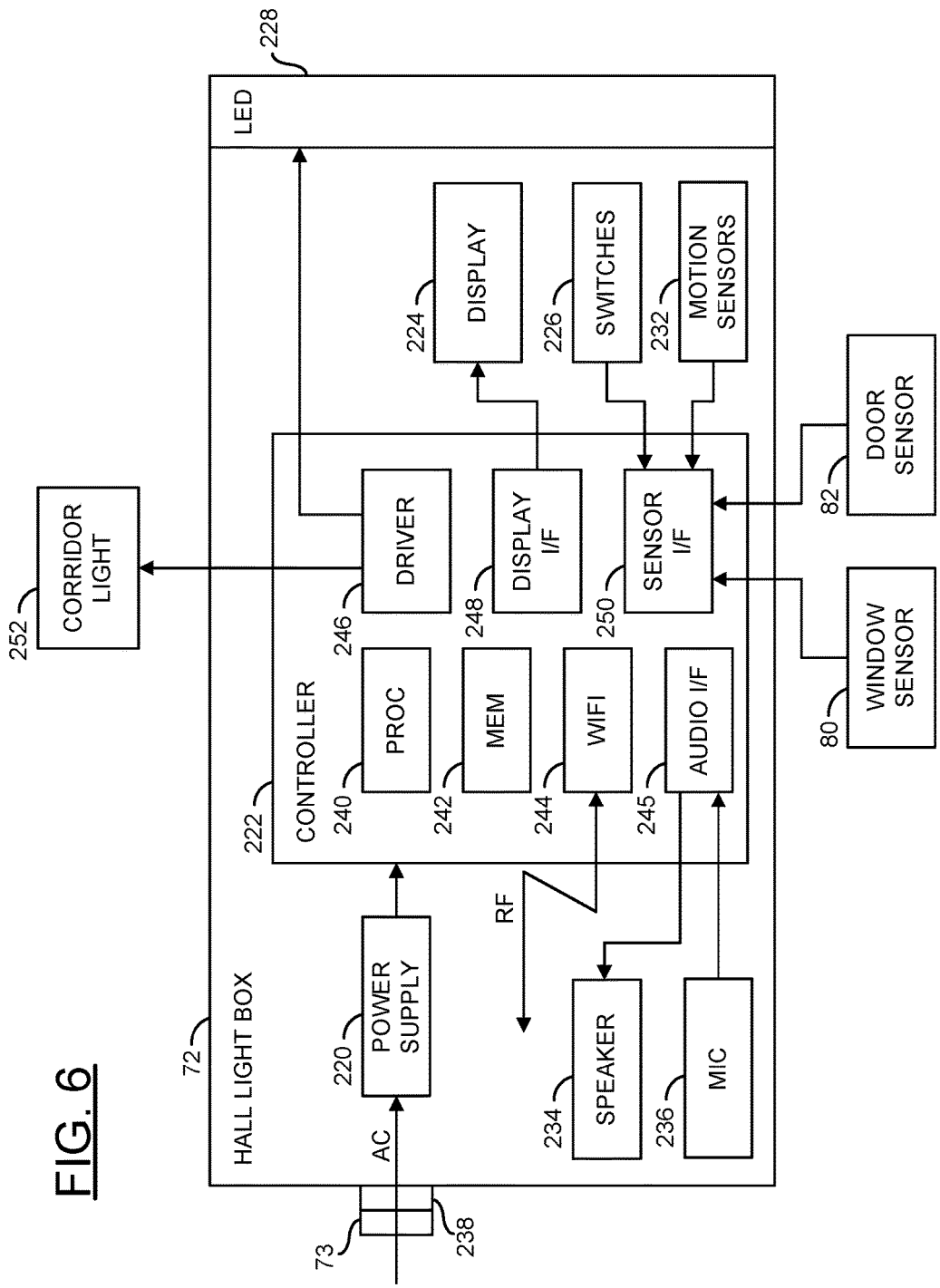
FIG. 6 is a diagram of the hall light box.

Referring to FIG. 6, a diagram of an example implementation of the hall light box 72 is shown. The hall light box 72 generally comprises a block (or circuit) 220, a block (or circuit) 222, a block (or circuit) 222, the display 224, the switches 226, the hall indicator 228, a block (or circuit) 232, a block (or circuit) 234, a block (or circuit) 236 and a block (or circuit) 238. The circuit 222 generally comprises a block (or circuit) 240, a block (or circuit) 242, a block (or circuit) 244, a block (or circuit) 245, a block (or circuit) 246, a block (or circuit) 248, a block (or circuit) 250. An optional block (or circuit) 252 may be connected to the circuit 222 and remotely located away from the housing of the hall light box 72. The circuits 220-252 may represent modules and/or blocks, embodiments of which include one or more of hardware circuitry and executable code (e.g., software, microcode, programming instructions, firmware, etc.) in a storage device used by the hardware circuitry. The hall light box 72 may be removably coupled to multiple blocks (or circuits) 73.

The circuits 73 may implement multiple electrically conductive (e.g., metal) standoffs (or plates). The standoffs 73 may be mounted to the walls of the facility at locations where a hall light box 72 is to be located. In some embodiments, the standoffs 73 may be operational to provide electrical power to the hall light boxes 72 when attached.

The circuit 220 may implement a power supply circuit. The power supply may receive the signal AC carrying alternating current electrical power. The power supply circuit 220 may be operational to convert the AC power to DC power. The DC power may be presented to the circuit 222.

The circuit 222 may implement a controller circuit. The controller 222 is generally operational to control the flow of information and operations of the hall light box 72. In various embodiments, the controller 222 may include one or more processors that implement a portion of the functionality of the hall light box 72 in software (or code or firmware).

The circuit 224 may implement a display circuit. The display 224 may be operational to present alphanumeric and/or graphic information. In various embodiments, the display 224 may be implemented as a liquid crystal display. In some embodiments, the display 224 may include a touch screen capability. The alphanumeric information may include general information (e.g., date, time, one or more resident names, etc.) In some embodiments, the alphanumeric information may include a name of a highest priority active alarm (e.g., BLUE, INTR, or CALL). The graphic information may include general information (e.g., weather symbols, animations, etc.). In various embodiments, the graphic information may include a graphic symbol for either the highest priority active alarm or multiple symbols for multiple active alarm. The color of the textual information and/or graphical information for the active alarms may change color over time as the duration of the active alarm lengthens.

The circuit 226 may implement a set of switches. The switches 226 may include, but are not limited to an intermediate switch, a code blue switch, a call switch, a work order switch, a dietary order switch, a suggestions switch, an ask-a-nurse switch, a request-to-reserve-a-room switch, and an information assistance switch. Other switches may be implemented to meet the design criteria of a particular application.

The circuit 228 may implement a hall indicator. In various embodiments, the hall indicator 228 may be implemented as multiple light-emitting diodes (LEDs). The hall indicator 228 may be located on two or more sides (e.g., at least the vertical sides) of a frame of the hall light box 72 such that the hall indicator 228 is visible from up and down the hall. The hall indicator 228 may be used in place of common corridor nurse call light indicators to help give the facilities a less institutional appearance.

The circuit 232 may implement one or more motion detector circuits. Each motion detector 232 may be operational to detect motion near the corresponding hall light box 72. In some embodiments, to conserve the useful life of the displays 224 of the hall light boxes 72, the processor 240 may use data from the motion detectors 232 to control the corresponding display 224. When little or no motion has been sensed by the motion detectors 232 for a predetermined time, the processor 240 may dim or power down (e.g., low power or no power) the display 224. When motion toward the hall light box 72 is sensed, the processor may brighten or power up the display 224.

The circuit 234 may implement a speaker. The speaker 234 is generally operational to generate audible sounds. The audible sounds may include verbal messages and/or tones. In some situations, the verbal messages may be prerecorded messages. In other situations, the verbal messages may be live messages. The tones may be sounded upon the activation of the code blue alarms, the intermediate alarms and/or the regular (or normal) alarms. The tones may be prioritized such that the higher-priority tones are sounded in favor of the lower-priority tones. The tones may change over time while the highest-priority alarm remains active. The tones may be extinguished after all of the alarms have been cancelled.

The circuit 236 may implement a microphone. The microphone 236 may be operational to record sounds from the environment around the hall light box 72. The sounds may be available to the internal circuitry and software programs of the hall light box 72, such as the information assistant capability. In various embodiments, the microphone 236 may be implemented as an omnidirectional microphone.

The circuits 238 may implement multiple magnets. The magnets 238 may be operational to hold the hall light box 72 to a wall via the standoffs 73. Two or more of the standoff/magnet pairs 73/238 may be operational to transfer electrical power to the power supply 220. In some embodiments, additional standoff/magnet pairs 73/238 may be provided to increase the mechanical support without transferring electrical power. Use of the standoffs/magnets 73/238 generally allows for easy removal and replacement of a hall light box 72.

The circuit 240 may implement one or more processors (one shown). The processor 240 is generally operational to execute software to control the workings of the hall light box 72. The circuit 242 may implement a memory circuit. The memory 242 is generally operational to store the software executed by the processor 240. In various embodiments, the memory 242 may be used to buffer information gathered by the hall light box 72 but not yet transmitted to the annunciator 62 and/or the server computer 64. In some embodiments, part or all of the memory 242 may be implemented as nonvolatile memory.

The circuit 244 may implement a wireless transceiver circuit. The wireless transceiver 244 may be operational to provide bidirectional communications between the hall light box 72 and two or more corresponding (or nearest) call light boxes 100a-100n, the server computer 64 and the annunciator 62.

The circuit 245 may implement an audio interface circuit. The audio interface circuit 245 may be operational to receive electrical signals generated by the microphone 236. The audio interface circuit 245 may also be operational to generate electrical signals that drive the speaker 234.

The circuit 246 may implement a driver circuit. The driver circuit 246 is generally operational to provide electrical power to the light source 228 and the circuit 252.

The circuit 248 may implement a display interface circuit. The display interface circuit 248 may be operational to control the display 224. Where the display 224 includes the touch screen capability, the display interface circuit 248 may be operational to provide the touch screen entries to the processor 240.

The circuit 250 may implement a sensor interface circuit. The sensor interface circuit 250 may be operational to sense the status of the switches 226. The sensor interface circuit 250 may also be operational sense the statuses of a window sensor 80 and a door sensor 82.

The circuit 252 may implement an optional corridor light. The corridor light 252 may be located high on a hall wall proximate a door of a room. The corridor light 252 is generally implemented where the light source 228 is not easily viewed from far away in the hall.

The window sensor 80 may be operational to determine if a window is open past a predetermined distance (e.g., greater than 4 inches). The window sensor 80 may be used with normal window resistance to discourage the residents from opening the window too far, but not enough resistance to not allow evacuation of the room through the window. In various embodiments, the window sensor 80 may be hardwired to the corresponding hall light box 72.

The door sensor 82 may be operational to determine if the door to the room is open or closed. The door sensor 82 generally does not offer any resistance to opening and closing the door. In various embodiments, the door sensor 82 may be hardwired to the corresponding hall light box 72.

In various embodiments, the door sensor 82 may also be operational to detect motion through a doorway. When the door sensor 82 identifies a movement through the doorway, the door sensor 82 may send a motion message to the corresponding hall light box 72. The hall light box 72 may interpret the motion message as a resident and/or another person moving from the hallway to the residential room, from the residential room to the hallway, from the bedroom to the bathroom and from the bathroom to the bedroom. The hall light box 72 may subsequently send a message to the annunciator 62 and/or the server computer 64 that movement in a particular direction at a given time was been detected. The server computer 64 may log the motion. The log may be useful when trying to locate a subsequently missing resident/patient.

Figure 7:
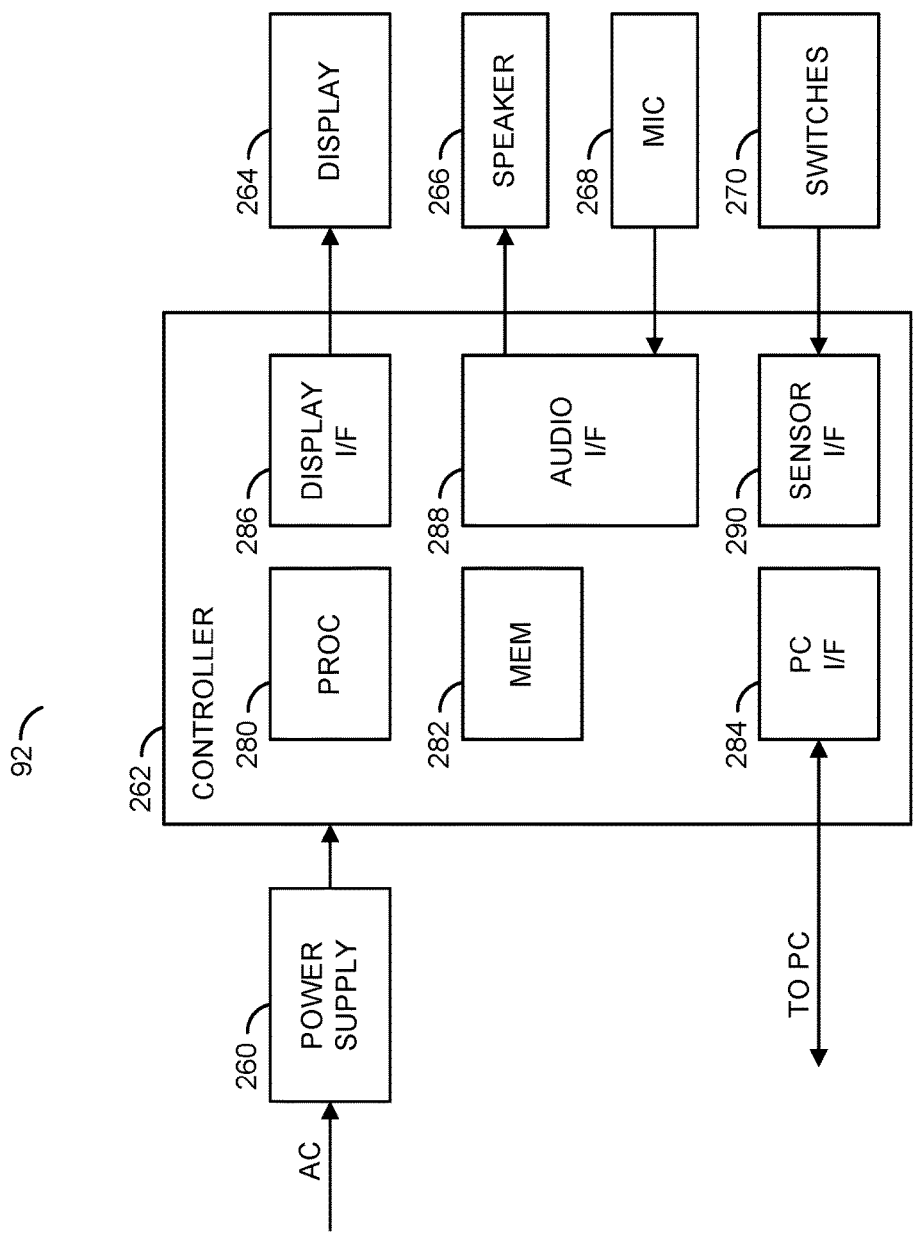
FIG. 7 is a diagram of an annunciator display.

Referring to FIG. 7, a diagram of an example implementation of the annunciator display 92 is shown. The annunciator display 92 generally comprises a block (or circuit) 260, a block (or circuit) 262, a block (or circuit) 264, a block (or circuit) 266, a block (or circuit) 268 and a block (or circuit) 270. The circuit 262 generally comprises a block (or circuit) 280, a block (or circuit) 282, a block (or circuit) 284, a block (or circuit) 286, a block (or circuit) 288 and a block (or circuit) 290. The circuits 260-290 may represent modules and/or blocks, embodiments of which include one or more of hardware circuitry and executable code (e.g., software, microcode, programming instructions, firmware, etc.) in a storage device used by the hardware circuitry.

The circuit 260 may implement a power supply circuit. The power supply may receive the signal AC carrying alternating current electrical power. The power supply circuit 260 may be operational to convert the AC power to DC power. The DC power may be presented to the circuit 262.

The circuit 262 may implement a controller circuit. The controller 262 is generally operational to control the flow of information and operations of the annunciator display 92. In various embodiments, the controller 262 may include one or more processors that implement a portion of the functionality of the annunciator display 92 in software (or code or firmware).

The circuit 264 may implement a display circuit. The display 264 is generally operational to present visual status information for each room to staff members. In various embodiments, the visual information may be presented in the form of a list. The list may show higher priority active alarms in lines nearest the top. A color of each line may change over time the longer an alarm is active.

The circuit 266 may implement one or more speakers (one shown). The speaker 266 is generally operational to present acoustic status information for each room to staff members. In various embodiments, the acoustic information may be presented in the form of tones or prerecorded messages from the display. The tones/messages may be different from each other to uniquely identify the different types of active alarms. The tones/messages may change over time the longer an alarm is active.

The circuit 268 may implement a microphone. The microphone 268 may be operational to record sounds from the environment around the nurse station 61. In various embodiments, the microphone 268 may be implemented as a directional microphone to emphasize a voice of a person in front of the annunciator display 92.

The circuit 270 may implement a set of switches. The switches 270 are generally operational to provide for manual input commands to the annunciator display 92. The switches 270 may include, but are not limited to, a push-to-talk switch, a display brightness adjustment, an audio level adjustment and a remote active call light cancellation switch. Other switches may be implemented to meet the design criteria of a particular application.

The circuit 280 may implement one or more processors (one shown). The processor 280 is generally operational to execute software to control the workings of the annunciator display 92.

The circuit 282 may implement a memory circuit. The memory 282 is generally operational to store the software executed by the processor 280. In various embodiments, the memory 282 may be used to buffer information gathered by the annunciator display 92 but not yet transmitted to the call light boxes 100a-100n and/or the hall light box 72. In some embodiments, part or all of the memory 282 may be implemented as nonvolatile memory.

The circuit 284 may implement a personal computer interface circuit. The personal computer interface circuit 284 may be operational to provide bidirectional communications with the personal computer 90. In various embodiments, the personal computer interface circuit 284 may be implemented as a wired network (e.g., Ethernet or a USB network) or a wireless network (e.g., wireless Ethernet or Wi-Fi)

The circuit 286 may implement a display interface circuit. The display interface circuit 286 may be operational to control the display 264.

The circuit 288 may be implemented an audio interface circuit. The audio interface circuit 288 may be operational to receive electrical signals generated by the microphone 268. The audio interface circuit 288 may also be operational to generate electrical signals that drive the speaker 266.

The circuit 290 may implement a sensor interface circuit. The sensor interface circuit 290 may be operational to sense the status of the switches 270.

Figure 8:
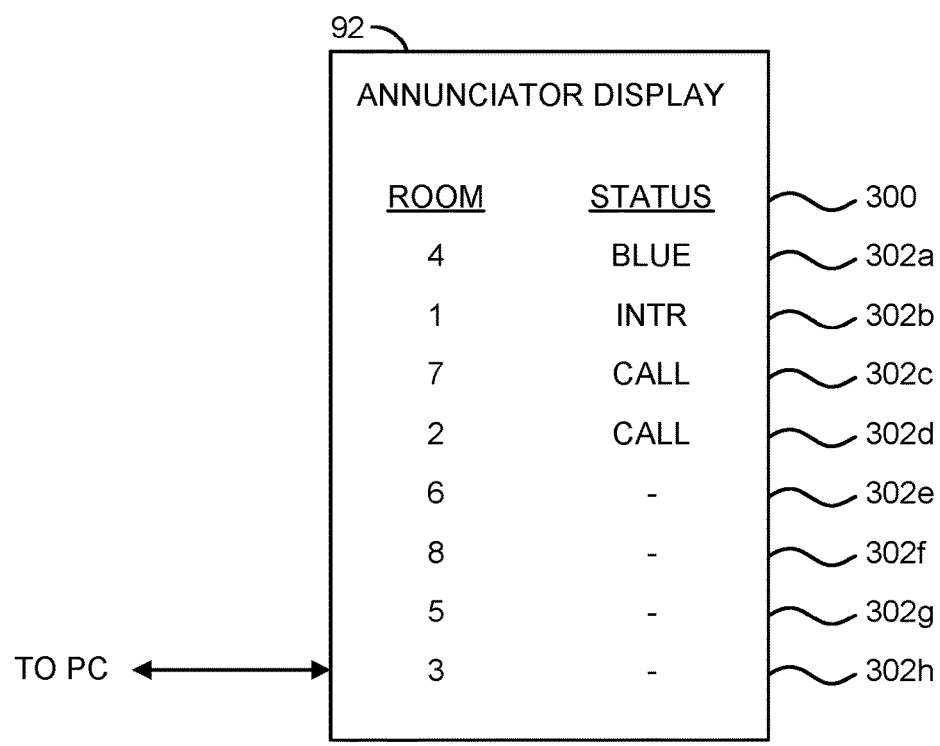
FIG. 8 is an example image displayed at the annunciator display.

Referring to FIG. 8, an example image displayed on the annunciator display 92 is shown. The image may be in the form of list having a header line 300 and multiple status lines 302a-302h. The lines 300 and 302a-302h may be arranged in multiple (e.g., two) columns. A header in a left column of the header line 300 may be the word "ROOM". A header in a right column of the header line 300 may be the word "STATUS". Each line 302a-302h in the column ROOM may include a respective room number (e.g., room 1 to room 8). Each line 302a-302h in the column STATUS may include an alphanumeric phrase and/or graphic symbol. In various embodiments, the phrase "BLUE" may be used to indicate that a code blue alarm is active in the associated room (e.g., room 4 in the example). The phrase "INTR" may be used to indicate that an intermediate alarm is active in the associated rooms (e.g., room 1 in the example). The phrase "CALL" may be used to indicate that a normal alarm is active in the associated rooms (e.g., the rooms 7 and 2 in the example). A character or symbol (e.g., a dash) may be used to indicate that no alarms are active in the associated rooms (e.g., rooms 6, 8, 5 and 3 in the example).

The list may be a dynamic list generated by the processor 280 and the display interface 286. The highest-priority active alarms (e.g., the code blue alarms) may be placed at the top of the list with the active code blue alarms ordered by oldest on top followed by next oldest alarms below. Below the newest code blue phrase, if any, the active intermediate-level alarms may be displayed. The active intermediate alarms may be organized based on the age of the alarms, oldest above and newest below. Below the newest code blue alarm, if any, and the newest intermediate alarm, if any, are the active normal alarm phrases. The normal alarms may be ordered with the oldest on top and the newest below. Any rooms not having an active alarm may be indicated with the dash character/symbol or a blank space.

The locations of the active alarms may be changed and updated as active alarms are canceled. For example, if the code blue alarm in room 4 is canceled, the room 4 may be moved to a bottom of the list and all other rooms moved up a line in the list. Adding a new alarm (e.g., an intermediate alarm from room 5) may cause the list to be adjusted such that the intermediate alarm from room 5 is positioned below the older intermediate alarm from room 1 and above the older normal alarm from room 7.

As a duration of each active alarm gets longer, the text and/or symbols for the active alarms may be changed in time. In various embodiments, the color of the alarms may change over time. For example, new active alarms may be shown in white while old active alarms may be shown in red. In some embodiments, the older alarms may be highlighted by increasing a size of the text/symbols, bolding, underlining and/or flashing the text/graphics.

Figure 9:
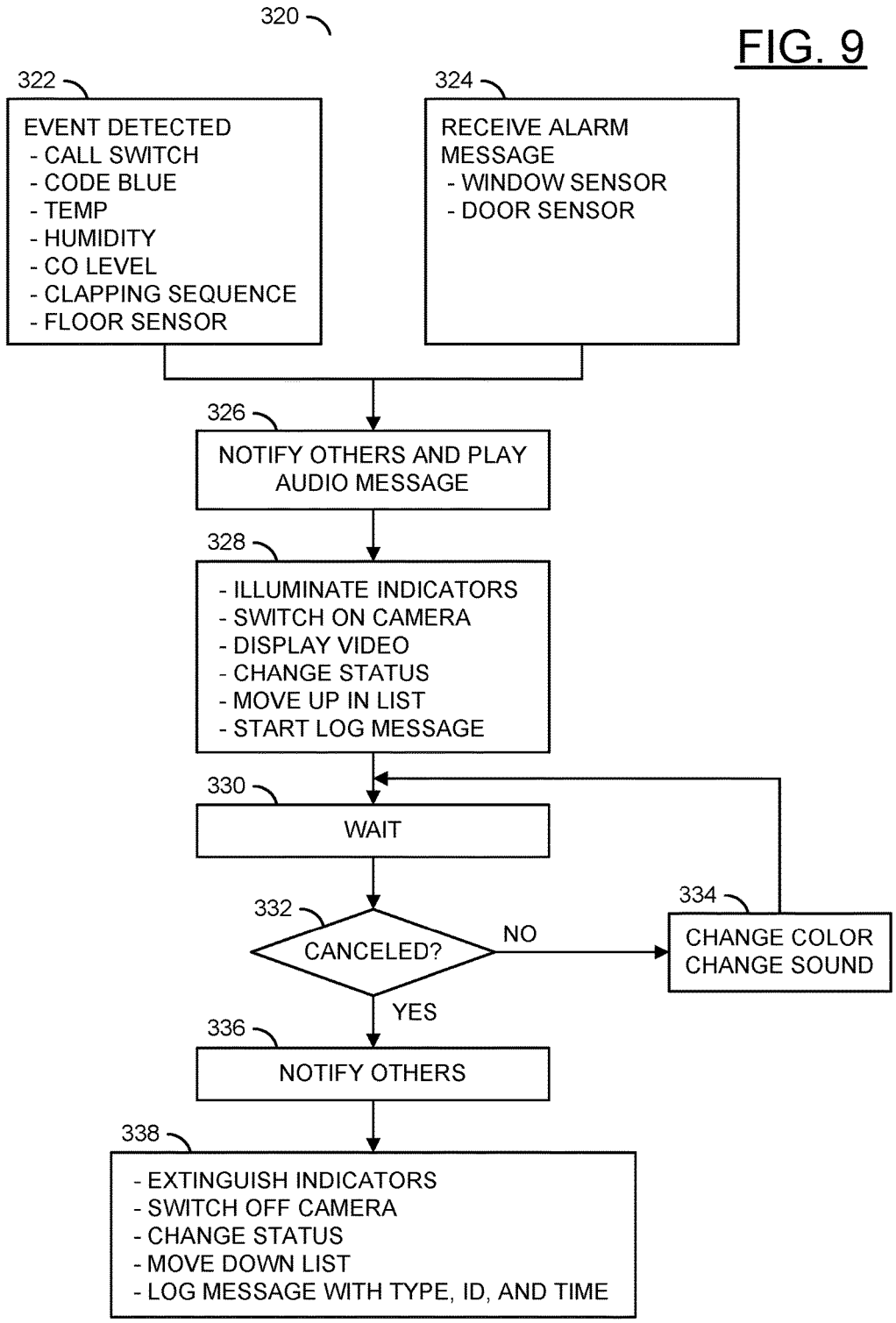
FIG. 9 is a flow diagram of an active event.

Referring to FIG. 9, a flow diagram of an example of a method 320 for processing an active event is shown. The method (or process) 320 may be implemented in the system 60. The method 320 generally comprises a step (or state) 322, a step (or state) 324, a step (or state) 326, a step (or state) 328, a step (or state) 330, a step (or state) 332, a step (or state) 334, a step (or state) 336 and a step (or state) 338.

The sequence of the steps is shown as a representative example. Other step orders may be implemented to meet the design criteria of a particular application.

In the step 322, an event may be detected by the call light box 100x. The event may be any one or more of a switch activation or a sensor detecting a level out of range. The switches may include, but are not limited to, the call switch 126, the intermediate switch 116, the code blue switch 122, the magnetic switch 202 and the floor sensor 76. Sensed level may include, but are not limited to a temperature in the room departing from a specified range (e.g., too hot or too cold), a humidity in the room departing from a specified range (e.g., too humid or too dry), a carbon monoxide level exceeding a threshold and a clapping sequence being detected by the microphone 108. In various embodiments, the clapping sequence may be two claps to trigger the alarm so that the resident far from the nearest call light box 100a-100n does not have to access a pendant or other electronic device to trigger a call.

In the step 324, the call light box 100x may receive an alarm message from the hall light box 72 across the wireless network. The alarm messages may include, but are not limited to, the window sensor 80 being triggered because a corresponding window is opened too far and the door sensor 82 being triggered because a corresponding door is open when it should be closed (e.g., 3 am).

In response to an event detected locally or the reception of the alarm message from the corresponding hall light box 72, the call light box 100x may notify other components in the system in the step 326 with an alarm message. The other components notified may include the annunciator 62, the server computer 64, the corresponding hall light box 72 and the pager station 74. In various embodiments, the server computer 64 may generate an email to one or more members of the staff members to notify that the event has occurred.

The call light box 100x may also play an audio recorded message in the step 326 to notify the resident that the alarm has been acknowledged and is being processed. For example, the audio recorded message may state "Your call light has been activated, your staff assistant will be with you shortly." In another example, the audio recorded message may be recorded by a family member, such as "Mom, I am sorry I am not there right now, but your call light has been activated and your staff assistant will be there shortly." The messages may be in English, French, Spanish, German or any other language. Other types of audio messages may be implemented to meet the design criteria of a particular application.

The call light box 100x, the corresponding hall light box 72 and the annunciator 62 may all illuminate a respective alarm indicator in the step 328. The annunciator 62 may move the room initiating the call up in the list based on priority and timing relative to other active calls. The status for the room shown by the annunciator 62 may also be changed to match the type of alarm activated.

If the event is an activation of the code blue switch 122, the call light box 100x may also switch on the camera 120 and stream live video to the annunciator 62. In some embodiments, the call light box 100x does not record the live video stream. The annunciator 62 generally displays the live video stream on the annunciator display 92 and/or a computer screen of the personal computer 90. The server computer 64 may start a log entry indicting the time, the room and the type of alarm activated.

In the step 330, the call light box 100x, the hall light box 72 and the annunciator 62 may wait for a period to see if the alarm is being handled. A check may be performed in the step 332 to determine if a staff member has swiped an identification card across the card reader 104. If not, the call light box 100x, the hall light box 72 and the annunciator 62 may change the color of the active alarm and/or change the alarm sound to indicate that the alarm has been active for a single period. The method 320 may return to the step 330 and wait a second period. Each time a period ends, if the alarm remains active, the call light box 100x, the hall light box 72 and the annunciator 62 may again alter the alarm color and/or alarm sound.

Once the card reader 104 has received an authorized identification number (e.g., a janitor may not be authorized to cancel a code blue alarm), the call light box 100x may notify the other components of the system 60 that the alarm has been answered. In various embodiments, the call light box 100x may send a cancel message to the hall light box 72, the annunciator 62 and the server computer 64. The cancel message generally contains the room number, the authorized identification number of the staff member that answered the call and a time that the card was swiped.

In response to the alarm being answered, the call light box 100x may switch off the camera 120, if on, in the step 338. Furthermore, the call light box 100x, the hall light box 72 and the annunciator 62 may extinguish the alarm indicators. The annunciator 62 may change the status of the room to no alarm. The server computer 64 may update a log of the alarm to include an end time and the authorized identification number used to answer the alarm.

Some or all call light activations and cancellations may be logged by the server computer 64 and accessible through the Internet. The logs generally contain the room number, type of alarm, time stamps and who answered the alarms (e.g., the badge identification number). The alerts may also trigger the server computer 64 to send emails to certain staff members (e.g., general managers, Director of Health Services, Director of Nursing, etc.) The emails may be sent in predetermined time frames (e.g., daily, weekly). The emails may detail call lights that took longer than a predetermined time to answer (e.g., 10 minutes or longer).

Figure 10:
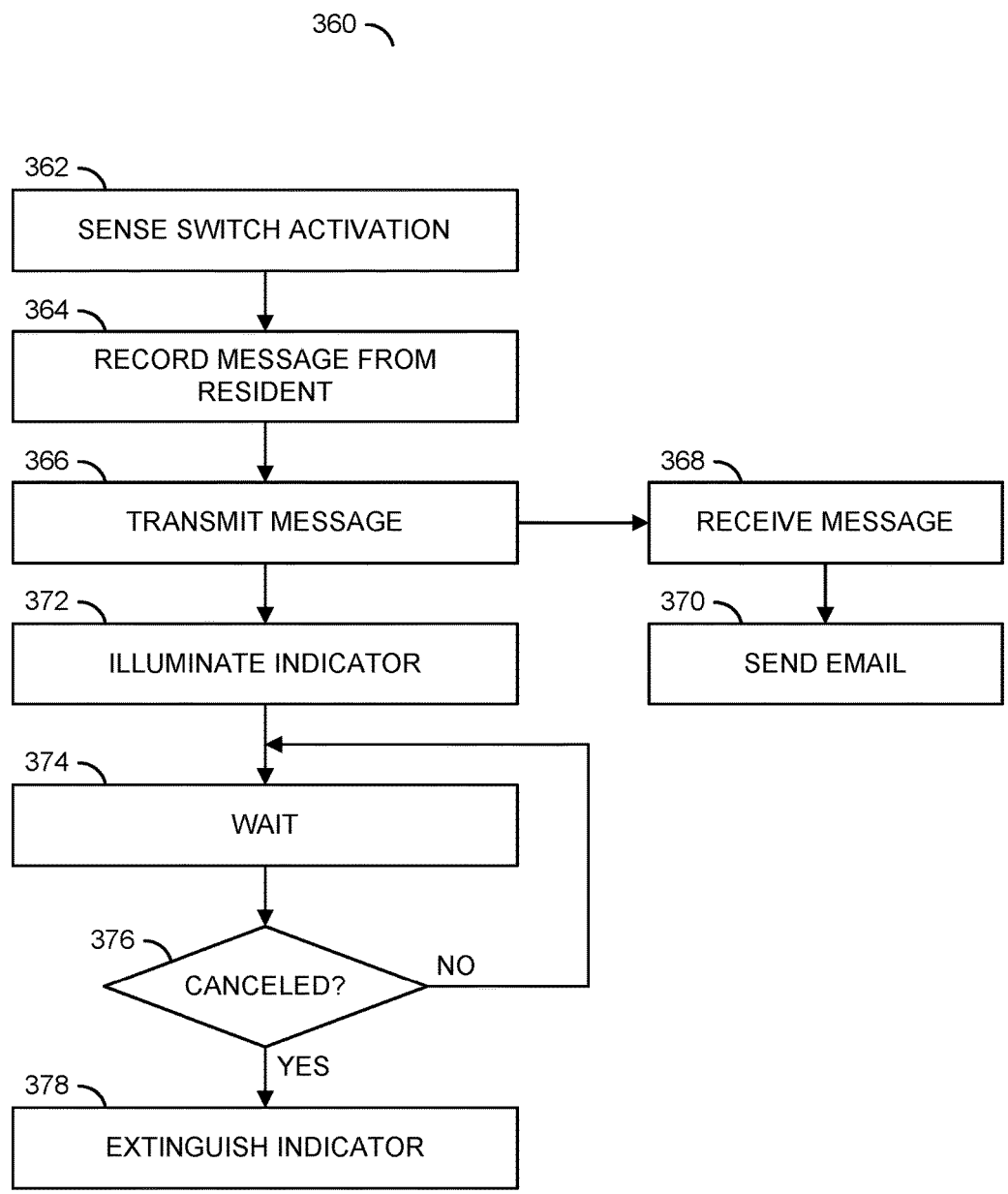
FIG. 10 is a flow diagram of a service request.

Referring to FIG. 10, a flow diagram of an example method 360 for processing a service request is shown. The method (or process) 360 may be implemented by the system 60. The method 360 generally comprises a step (or state) 362, a step (or state) 364, a step (or state) 366, a step (or state) 368, a step (or state) 370, a step (or state) 372, a step (or state) 374, a step (or state) 376 and a step (or state) 378. The sequence of the steps is shown as a representative example. Other step orders may be implemented to meet the design criteria of a particular application.

In the step 362, the call light box 100x or a hall light box 72 may sense an activation of a service switch 110 (e.g., the work switch 112/226 or the dietary switch 114/226). The call light box 100x or hall light box 72 may record an audio message from the resident in the step 364. In the step 366, the call light box 100x or the hall light box 72 may transfer the audio message and an intended destination (e.g., the maintenance area or the kitchen area) to the server computer 64 via the wireless network. Upon reception of the audio message, the server computer 64 may generate and send an email to either the maintenance staff or the kitchen staff as notification for the waiting message. The audio message may be stored in a secure website (e.g., the server computer 64). Upon receipt of the email, the service staff may access the recorded message with propr authorization from the secure website and respond to the audio message. The secure website may be accessible from kiosks (e.g., the kitchen computer 66 and the maintenance computer 68) located in both the maintenance shop area and in the dietary area.

In the step 372, the call light box 100x or the hall light box 72 may illuminate a service-requested type of indicator (e.g., a yellow text and/or symbol) on the display 106/224 to acknowledge that the request has been sent. In some embodiments, the call light box 100x may send a message to the hall light box 72 to illuminate a similar service-requested indicator. The call light box 100x or the hall light box 72 may subsequently wait for a suitable period in the step 374 to see if the request has been fulfilled.

A check may be performed in the step 376 to determine if an authorized staff member has swiped an identification card across the card reader 104. If not, the call light box 100x (and possibly the hall light box 72) may change the color (e.g., yellow to orange) of the service-requested indicator to show that the request has been active for a single period. The method 360 may return to the step 374 and wait a second period. Each time a period ends, if the request remains unfulfilled, the call light box 100x (and possibly the hall light box 72) may again alter the service request indicator (e.g., orange to red).

Figure 11:
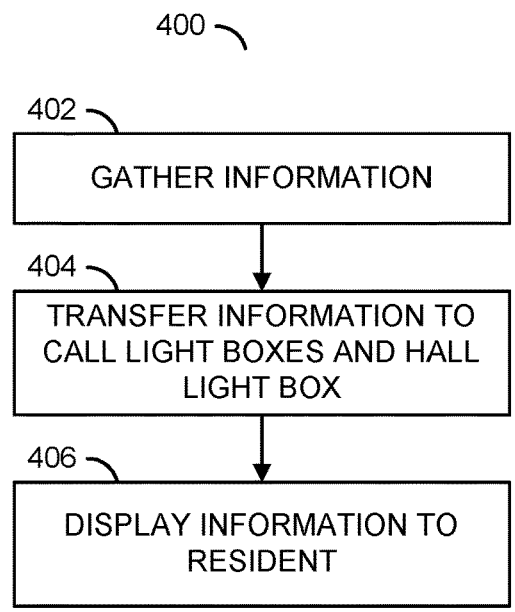
FIG. 11 is a flow diagram of an information transfer.

Referring to FIG. 11, a flow diagram of an example method 400 for information transfers is shown. The method (or process) 400 may be implemented by the system 60. The method 400 generally comprises a step (or state) 402, a step (or state) 404 and a step (or state) 406. The sequence of the steps is shown as a representative example. Other step orders may be implemented to meet the design criteria of a particular application.

In the step 402, the server computer 64 and/or the annunciator 62 may gather information relevant to one or more residents. The information may include, but is not limited to, a weather forecast, a kitchen menu, announcements for planned activities, birthdays, holidays, and the like. In some situations, the information may be gathered automatically (e.g., the weather) by the server computer 64. In other situations, a receptionist may enter information (e.g., special notices) and the information may be immediately presented throughout the building.

By way of example, a welcome message may appear on the digital display of the hall light box 72 outside a resident's room upon admission. The welcome message may cycle for several (e.g., 36) hours, afterwards may message may automatically stop. The welcome message may be replaced by a resident/patient name on the display. In various embodiments, a short biography can scroll on the displays of the call light boxes 100a-100n and/or hall light boxes 72. Furthermore, background pictures and/or animated videos may cycle through any one or more themes, such as sunsets, outdoor scenes, dogs, city-scapes, and the like. The pictures and video clips may include family photographs. The displays of the call light boxes 100a-100n and/or the hall light boxes 72 may include colored dots on the displays to indicate if the residents/patients that have allergies, are diabetic, have special conditions, and the like. When a room is empty, the hall light boxes 72 may display a vacancy-type message in place of resident/patient names to indicate the current status of the room. The vacancy-type messages may include, but are not limited to, a "maintenance hold" message so that the maintenance staff may touch up the room prior to a next resident/patient, and a "welcome" message when the room is ready for a newly admitted resident/patient.

The information may be transferred in the step 404 to the call light boxes 100a-100n and/or the hall light boxes 72. In the step 406, the call light boxes 100a-100x and the hall light boxes 72 may display the information to the residents.

Figure 12:
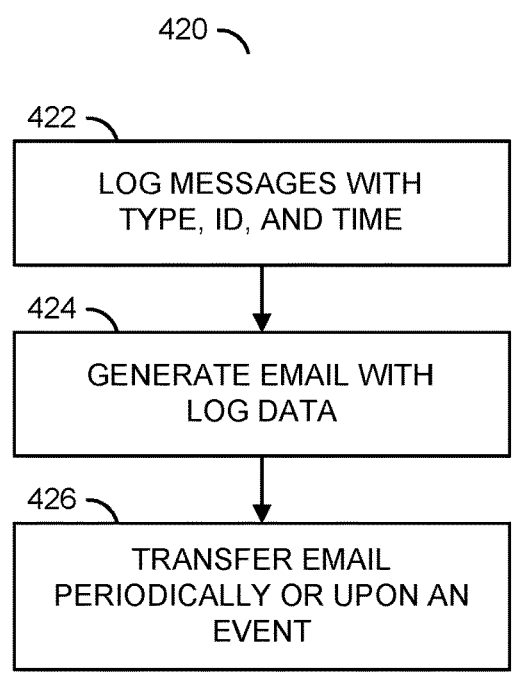
FIG. 12 is a flow diagram of a log generation.

Referring to FIG. 12, a flow diagram of an example method 420 for log generation is shown. The method (or process) 420 may be implemented by the system 60. The method 420 generally comprises a step (or state) 422, a step (or state) 424 and a step (or state) 426. The sequence of the steps is shown as a representative example. Other step orders may be implemented to meet the design criteria of a particular application.

In the step 422, the server computer 64 may generate log messages for each active event and/or service request. The logs generally identify the initiating room number, the initiating time, the authorized identification number of the staff member that responded to the event and/or service request and a time of the response. The server computer 64 may generate one or more emails with the log messages in the step 424. Different emails with different types of log messages (e.g., all maintenance requests, all code blue alerts, all dietary requests, and the like) may be created. In the step 426, the emails with the corresponding log messages may be transferred periodically and/or upon an event (e.g., all code blue alert log messages may be emailed as soon as the alert is ended).

Figure 13:
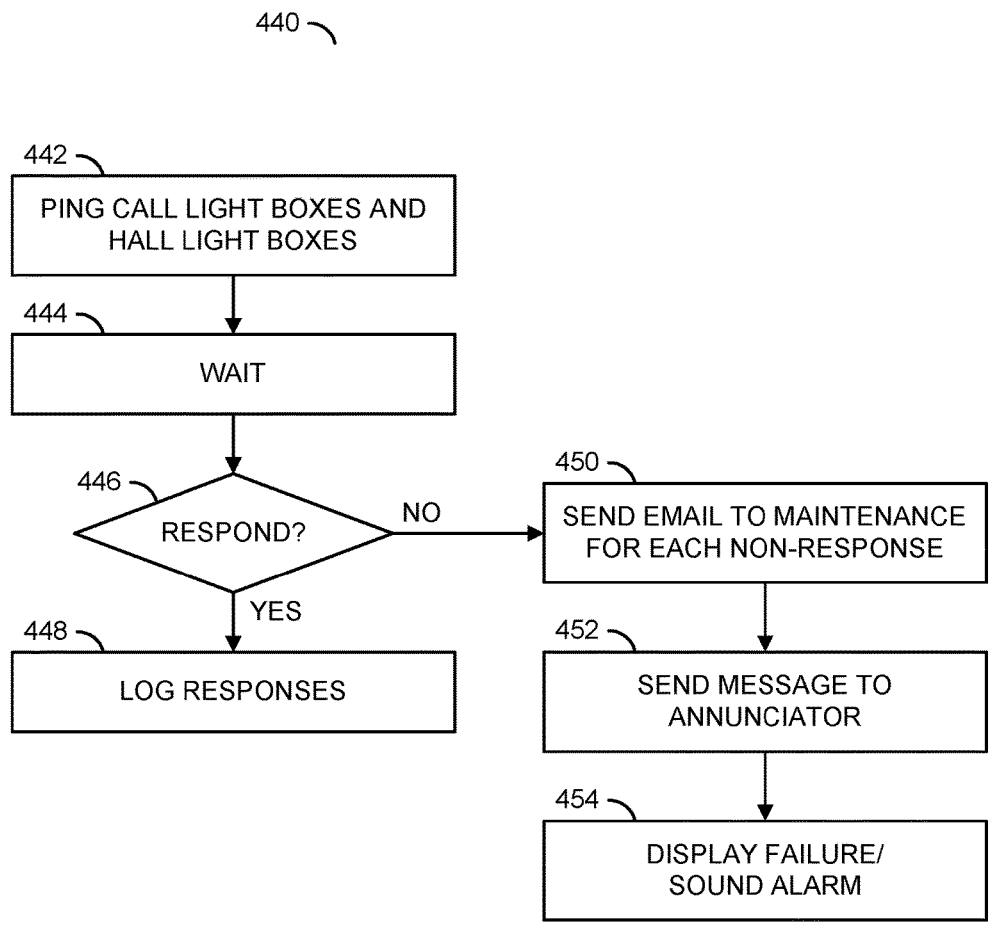
FIG. 13 is a flow diagram of a self test in the system.

Referring to FIG. 13, a flow diagram of an example method 440 for self test in the system 60 is shown. The method (or process) may be implemented by the system 60. The method 440 generally comprises a step (or state) 442, a step (or state) 444, a step (or state) 446, a step (or state) 448, a step (or state) 450, a step (or state) 452 and a step (or state) 454. The sequence of the steps is shown as a representative example. Other step orders may be implemented to meet the design criteria of a particular application.

In the step 442, the server computer 64 may ping all of the call light boxes 100a-100n, all of the hall light boxes 72 and all of the annunciators 62 with a query message via the wireless network. The query messages may be sent in parallel, in sequence, or any combination thereof. The server computer 64 may wait for an appropriate amount of time in the step 444 for the call light boxes 100a-100n, the hall light boxes 72 and the annunciators 62 to respond to the query message with a status message. The response of each call light box 100a-100n, each hall light box 72 and each annunciator 62 may be considered individually by the server computer 64 in the step 446. For each call light box 100a-100n, each hall light box 72 and each annunciator 62 that properly responds with a status message, the server computer 64 may generate a log entry of the proper responses in the step 448.

For each call light box 100a-100n, each hall light box 72 and each annunciator 62 that fails to respond within a time limit, or responds improperly, the server computer 64 may generate and send an email message to the maintenance computer 68 and/or designated staff in the step 450. The email may identify the location (e.g., room number) of the box 62, 72/100a-100n that did not properly respond. In the step 452, the server computer 64 may send a message to a working annunciator 62 notifying the annunciator 62 of the improper response(s). The annunciator 62 may response to the message by displaying a failure phrase and/or icon in the appropriate room line on the annunciator display 92. In some embodiments, the annunciator 62 may also sound an alert message and/or tone to alert the staff to the failure.

In various embodiments, the system 60 may include door sensors and camera units at all of the exterior doors of the building and possibly some interior doors. The door sensors/camera units may enable the server computer 64 to record video of the doors at all times. When the door sensor is triggered by a person in proximity of the door, the server computer 64 may send an alert message and send several (e.g., 30) seconds of captured video to the annunciator 62 at the nurse station 61. The door sensor/camera unit may also sound alarm to distract a confused resident who is in danger of leaving the building through the door without an escort. In some designs, two door sensor units may be located at each designated door. If one of the door sensor units fails, the other door sensor unit may still work. By including the door sensor units in the list of devices periodically pinged by the server computer 64, any failure to properly respond may be detected, and an alert email may be automatically generated and sent to designated staff indicating that service is requested.

In some embodiments, the server computer 64 may use the identification badges to keep loose track of the locations of the staff members. For example, if a particular staff member swipes the card reader 104 in a particular room, the server computer 64 may record the particular staff in particular room at the time of the swipe. If an alert or other high-priority message is generated that should be brought to the attention of the particular staff member shortly after the swipe, the server computer 64 may direct the alert and/or high-priority message to the call light boxes 100*a*-100*n* and the hall light box 72 for the particular room. The particular staff member may acknowledge the alert/message by swiping the card reader 104 again and/or pressing the staff-only switch 118.

The functions and structures illustrated in the diagrams of FIGS. 1 to 13 may be designed, modeled, emulated, and/or simulated using one or more of a conventional general purpose processor, digital computer, microprocessor, microcontroller, distributed computer resources and/or similar computational machines, programmed according to the teachings of the present specification, as will be apparent to those skilled in the relevant art(s). Appropriate software, firmware, coding, routines, instructions, opcodes, microcode, and/or program modules may readily be prepared by skilled programmers based on the teachings of the present disclosure, as will also be apparent to those skilled in the relevant art(s). The software is generally embodied in a medium or several media, for example non-transitory storage media, and may be executed by one or more of the processors sequentially or in parallel.

Embodiments of the present invention may also be implemented in one or more of ASICs (application specific integrated circuits), FPGAs (field programmable gate arrays), PLDs (programmable logic devices), CPLDs (complex programmable logic device), sea-of-gates, ASSPs (application specific standard products), and integrated circuits. The circuitry may be implemented based on one or more hardware description languages. Embodiments of the present invention may be utilized in connection with flash memory, nonvolatile memory, random access memory, read-only memory, magnetic disks, floppy disks, optical disks such as DVDs and DVD RAM, magneto-optical disks and/or distributed storage systems.

The terms "may" and "generally" when used herein in conjunction with "is(are)" and verbs are meant to communicate the intention that the description is exemplary and believed to be broad enough to encompass both the specific examples presented in the disclosure as well as alternative examples that could be derived based on the disclosure. The terms "may" and "generally" as used herein should not be construed to necessarily imply the desirability or possibility of omitting a corresponding element.

While the invention has been particularly shown and described with reference to embodiments thereof, it will be understood by those skilled in the art that various changes in form and details may be made without departing from the scope of the invention.

The invention claimed is:

1. An apparatus comprising:
   a wireless transceiver configured to communicate wirelessly via a wireless network with (i) an annunciator remotely located from said apparatus and (ii) a plurality of call light boxes remotely located from said apparatus;
   a work order switch;
   a dietary order switch;
   a suggestion switch;
   an ask-a-nurse switch;
   a request-to-reserve-a-room switch; and
   a processor configured to (i) control reception of an alarm message from one or more of said call light boxes in response to an event, (ii) illuminate a hall indicator in response to reception of said alarm message, (iii) receive a cancellation message from at least one of (a) one or more of said call light boxes and (b) said annunciator that cancels said event, (iv) extinguish said hall indicator in response to cancellation of said event and (v) send a switch message to said annunciator with an indication of which one of (a) said work order switch, (b) said dietary order switch, (c) said suggestion switch, (d) said ask-a-nurse switch and (e) said request-to-reserve-a-room switch was activated, wherein said hall indicator changes color over time until said event is canceled.

2. The apparatus according to claim 1, wherein said apparatus is implemented as a hall light box in communication with a nurse station.

3. The apparatus according to claim 1, further comprising a plurality of magnets configured to (i) removably mount said apparatus to a wall and (ii) carry electrical power to said apparatus.

4. The apparatus according to claim 1, further comprising one or more motion sensors and a display, wherein
   said processor is further configured to both (i) activate said display in response to a motion detected by said motion sensors and (ii) deactivate said display a predetermined time after said motion is no longer detected.

5. The apparatus according to claim 1, wherein said processor is further configured to control (i) generation of an audible sound in response to said event and (ii) one or more changes to said audible sound over time until said event is canceled.

6. The apparatus according to claim 1, further comprising a display, wherein
   said processor is further configured to control presentation of said hall indicator as one or more of (i) a textual message, (ii) a graphic symbol or (iii) both on said display.

7. The apparatus according to claim 1, further comprising (i) a speaker, (ii) a microphone and (ii) a service indicator, wherein
   said processor is further configured to (i) play a prerecorded message through said speaker in response to sensing a service event, (ii) record sounds received through said microphone, (iii) control illumination of said service indicator, (iv) initiate a transfer of said sounds to a server computer via said wireless network and (v) control extinguishing of said service indicator.

8. The apparatus according to claim 1, further comprising a display, wherein
said processor is further configured to (i) receive information from one or more of (a) said annunciator, (b) a server computer or (c) both and (ii) control presentation of said information on said display.

9. The apparatus according to claim 1, further comprising a speaker,
wherein said processor is further configured to (i) control reception of a voice message from said speaker, (ii) relay said voice message to a server computer via said wireless network, (iii) receive a recorded message from said server computer and (iv) place said recorded message through said speaker.

10. The apparatus according to claim 1, further comprising (i) a microphone and (ii) a display,
wherein said processor is further configured to (i) control reception of a voice message from said microphone and (ii) change an indication on said display in response to said voice message.

11. A system comprising:
an annunciator located at a nurse station and comprising (i) a first display and (ii) a first processor configured to generate a list on said first display, wherein said list shows (a) a plurality of rooms and (b) a respective status of each of said rooms;
a server computer in communication with said annunciator via a wired network;
a plurality of call light boxes located in each of said rooms, wherein each of said call light boxes comprises (i) an alarm indicator, (ii) a card reader and (iii) a third processor; and
one or more hall light boxes located in one or more hallways outside each of said rooms, each of said hall light boxes comprising (i) a hall indicator and (ii) a second processor configured to control (a) communication via a wireless network with said annunciator and a corresponding set including one or more of said call light boxes, (b) illumination said hall indicator in response to reception of an alarm message from said corresponding set of said call light boxes, (c) changing a color of said hall indicator over time and (d) extinguishing said hall indicator in response to reception of a cancellation message from said corresponding set of said call light boxes, wherein
(A) said first processor in said annunciator is further configured to (i) change said status of said respective room to active on said first display in response to reception of said alarm message, (ii) move said respective room up in said list above said rooms where said respective status is inactive, (iii) change said status of said respective room to inactive on said first display in response to reception of said cancellation message and (iv) move said respective room down in said list below said rooms where said respective status is active in response to reception of said cancellation message,
(B) both (i) said hall indicators and (ii) said respective status on said first display of said annunciator change color over time until said cancellation message is received and
(C) said third processors in said call light boxes is each configured to (i) control communication via said wireless network with (a) said annunciator, (b) said server computer and (c) said hall light boxes, (ii) control transmission of said alarm message to all of (a) said annunciator, (b) said server computer and (c) said hall light boxes in response to an event, (iii) control illumination of said alarm indicator in response to said event, (iv) receive an authorized one of a plurality of identification numbers from said card reader, (v) initiate transmission of said cancellation message with said authorized identification number to all of (a) said annunciator, (b) said server computer and (c) said hall light boxes in response to reception of said authorized identification number while said event is active and (vi) control extinguishing of said alarm indicator in response to reception of said authorized identification number.

12. The system according to claim 11, wherein (i) each of said hall light boxes further comprises a frame and (ii) said hall indicator borders at least both vertical sides of said frame.

13. The system according to claim 11, wherein said server computer is configured to enter into a log (i) said respective room that sent said alarm message, (ii) a start time that said alarm message was received, (iii) said authorized identification number in said cancellation message from said respective room and (iv) an end time that said cancellation message was received.

14. The system according to claim 11, further comprising a pager station configured to (i) communicate with said call light boxes via said wireless network, (ii) receive a pager message from one of said call light boxes and (iii) send a page signal with said pager message to a corresponding one of a plurality of pagers.

15. The system according to claim 11, further comprising a service computer in communication with said annunciator through said wired network, wherein
each of said second processors in said hall light boxes are further configured to (i) record a verbal message and (ii) initiate transmission of said verbal message to said annunciator via said wireless network, and
said first processor in said annunciator is further configured to (ii) send an email with said verbal message to said service computer.

16. The system according to claim 11, wherein
(A) each of said hall light boxes comprises (i) a work order switch, (ii) a dietary order switch, (iii) a suggestion switch, (iv) an ask-a-nurse switch and (v) a request-to-reserve-a-room switch and
(B) each of said second processors is further configured to send a switch message to said annunciator with an indication of which one of (i) said work order switch, (ii) said dietary order switch, (iii) said suggestion switch, (iv) said ask-a-nurse switch and (v) said request-to-reserve-a-room switch was activated.

17. The system according to claim 16, wherein said annunciator is further configured to locate said respective room that send said switch message based upon which among (i) said work order switch, (ii) said dietary order switch, (iii) said suggestion switch, (iv) said ask-a-nurse switch and (v) said-request-to-reserve-a-room switch was activated.

18. The system according to claim 11, wherein each of said hall light box comprises:
a wireless transceiver configured to communicate wirelessly via said wireless network with (i) said annunciator remotely located from said hall light box and (ii) said call light boxes remotely located from said hall light box; and
said second processor configured to (i) control reception of said alarm message from one or more of said call light boxes in response to said event, (ii) illuminate said hall indicator in response to reception of said alarm message, (iii) receive said cancellation message from at least one of (a) said one or more of said call light boxes and (b) said annunciator that cancels said event, and (iv) extinguish said hall indicator in response to cancellation of said event, wherein said hall indicator changes color over time until said event is canceled.

\* \* \* \* \*